(12) United States Patent
Chan et al.

(10) Patent No.: US 10,577,247 B2
(45) Date of Patent: Mar. 3, 2020

(54) HYBRID NANOMATERIAL OF GRAPHENE OXIDE NANOMATERIAL AND CATIONIC QUATERNIZED CHITOSAN

(71) Applicant: Nanyang Technological University, Singapore (SG)

(72) Inventors: Bee Eng Mary Chan, Singapore (SG); Peng Li, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 204 days.

(21) Appl. No.: 14/776,600

(22) PCT Filed: Mar. 14, 2014

(86) PCT No.: PCT/SG2014/000125
§ 371 (c)(1),
(2) Date: Sep. 14, 2015

(87) PCT Pub. No.: WO2014/142757
PCT Pub. Date: Sep. 18, 2014

(65) Prior Publication Data
US 2016/0022827 A1 Jan. 28, 2016

Related U.S. Application Data

(60) Provisional application No. 61/791,784, filed on Mar. 15, 2013.

(51) Int. Cl.
| | | |
|---|---|---|
| *C01B 32/23* | (2017.01) | |
| *B82Y 5/00* | (2011.01) | |
| *A61K 31/722* | (2006.01) | |
| *B82Y 40/00* | (2011.01) | |
| *C08L 5/08* | (2006.01) | |
| *C08B 37/08* | (2006.01) | |
| *A61K 47/55* | (2017.01) | |
| *B82Y 30/00* | (2011.01) | |

(52) U.S. Cl.
CPC ............ *C01B 32/23* (2017.08); *A61K 31/722* (2013.01); *A61K 47/552* (2017.08); *B82Y 5/00* (2013.01); *B82Y 40/00* (2013.01); *C08B 37/003* (2013.01); *C08L 5/08* (2013.01); *B82Y 30/00* (2013.01); *Y02A 50/473* (2018.01)

(58) Field of Classification Search
None
See application file for complete search history.

(56) References Cited

FOREIGN PATENT DOCUMENTS

WO 2011/007454 A1 1/2011

OTHER PUBLICATIONS

Hu, W. et al., ACS Nano, Graphene-Based Antibacterial Paper, 2010, vol. 4, No. 7, 4317-4323.*
Akhavan et al., "Toxicity of Graphene and Graphene Oxide Nanowalls Against Bacteria," *ACS Nano* 4(10):5731-5736, 2010.
Bao et al., "Synthesis and characterization of silver nanoparticle and graphene oxide nanosheet composites as a bactericidal agent for water disinfection," *Journal of Colloid and Interface Science* 360(2):463-470, 2011.
Bao et al., "Chitosan-Functionalized Graphene Oxide as a Nanocarrier for Drug and Gene Delivery,", *Small* 7(11):1569-1578, 2011.
Becerril et al., "Evaluation of Solution-Processed Reduced Graphene Oxide Films as Transparent Conductors,", *ACS Nano* 2(3):463-470, 2008.
Cai et al., "Synergistic Antibacterial Brilliant Blue/Reduced Graphene Oxide/Quaternary Phosphonium Salt Composite with Excellent Water Solubility and Specific Targeting Capability," *Langmuir* 27(12):7828-7835, 2011.
Cao et al., "Reversibly Switching the Function of a Surface between Attacking and Defending against Bacteria," *Angewandte Chemie International Edition* 51:2602-2605, 2012.
Carpenter et al., "Dual Action Antimicrobials: Nitric Oxide Release from Quaternary Ammonium-Functionalized Silica Nanoparticles," *Biomacromolecules* 13:3334-3342, 2012.
Das et al., "Synthesis of silver nanoparticles in an aqueous suspension of graphene oxide sheets and its antimicrobial activity," *Colloids and Surfaces B: Biointerfaces* 83(1):16-22, 2011.
Dash et al., "Chitosan—A versatile semi-synthetic polymer in biomedical applications," *Progress in Polymer Science* 36(8):981-1014, 2011.
Dreyer et al., "The chemistry of graphene oxide," *Chemical Society Reviews* 39(1):228-240, 2010.
Eda et al., "Large-area ultrathin films of reduced graphene oxide as a transparent and flexible electronic material," *Nature Nanotechnology* 3(5):270-274, 2008.
Ellman, "Tissue Sulfhydryl Groups," *Archives of Biochemistry and Biophysics* 82(1):70-77, 1959.
Fowler et al., "Practical Chemical Sensors from Chemically Derived Graphene," *ACS Nano* 3(2):301-306, 2009.
Geim et al., "The rise of graphene," *Nature Materials* 6(3):183-191, 2007.
Hancock, "The bacterial outer membrane as a drug barrier," *Trends in Microbiology* 5(1): 37-42, 1997.
Hasan et al., "Antibacterial surfaces: the quest for a new generation of biomaterials," *Trends in Biotechnology* 31(5):295-304, 2013.
Hu et al., "Graphene-Based Antibacterial Paper," *ACS Nano* 4(7):4317-4323, 2010.

(Continued)

*Primary Examiner* — Layla D Berry
*Assistant Examiner* — Bahar Craigo
(74) *Attorney, Agent, or Firm* — Seed IP Law Group LLP

(57) ABSTRACT

A hybrid nanomaterial consisting of graphene oxide (GO) nanomaterial covalently conjugated to cationic quaternized chitosan is provided. Method of preparing the hybrid nanomaterial, an antimicrobial composition containing the hybrid nanomaterial, and use of the antimicrobial composition in inhibiting growth of microorganisms in an environment are also provided.

20 Claims, 18 Drawing Sheets

(56) References Cited

OTHER PUBLICATIONS

Hummers, Jr. et al., "Preparation of Graphitic Oxide," *Journal of the American Chemical Society* 80(6):1339, 1958.
Jung et al., "Effect of Water Vapor on Electrical Properties of Individual Reduced Graphene Oxide Sheets," *Journal of Physical Chemistry C* 112(51):20264-20268, 2008.
Kemény et al., "The Distribution of Cations in Plasma and Cerebrospinal Fluid Following Infusion of Solutions of Salts of Sodium, Potassium, Magnesium and Calcium," *Journal of Neurochemistry* 7:218-227, 1961.
Kovtyukhova et al., "Layer-by-Layer Assembly of Ultrathin Composite Films from Micron-Sized Graphite Oxide Sheets and Polycations," *Chemistry of Materials* 11(3): 771-778, 1999.
Latge, "The cell wall: a carbohydrate armour for the fungal cell," *Molecular Microbiology* 66(2): 279-290, 2007.
Lee et al., "Structural Determination and Interior Polarity of Self-Aggregates Prepared from Deoxycholic Acid-Modified Chitosan in Water," *Macromolecules* 31(2):378-383, 1998.
Li et al., "Processable aqueous dispersions of graphene nanosheets," *Nature Nanotechnology* 3(2): 101-105, 2008.
Li et al., "A polycationic antimicrobial and biocompatible hydrogel with microbe membrane suctioning ability," *Nature Materials* 10(2):149-156, 2011.
Li et al., "Soluble Reduced Graphene Oxide Functionalized with Conjugated Polymer for Heterojunction Solar Cells," *Journal of Polymer Science Part A: Polymer Chemistry* 50(9):1663-1671, 2012.
Li et al., "Antimicrobial macromolecules: synthesis methods and future applications," *RSC Advances* 2(10):4031-4044, 2012.
Li et al., "Cationic Peptidopolysaccharides Show Excellent Broad-Spectrum Antimicrobial Activities and High Selectivity," *Advanced Materials* 24:4130-4137, 2012.
Liao et al., "Cytotoxicity of Graphene Oxide and Graphene in Human Erythrocytes and Skin Fibroblasts," *ACS Applied Materials & Interfaces* 3(7):2607-2615, 2011.
Lim et al., "Facile preparation of graphene-based chitosan films: Enhanced thermal, mechanical and antibacterial properties," *Journal of Non-Crystalline Solids* 358(3):525-530, 2012.
Liu et al., "Antibacterial Activity of Graphite, Graphite Oxide, Graphene Oxide, and Reduced Graphene Oxide: Membrane and Oxidative Stress," *ACS Nano* 5(9):6971-6980, 2011.
Liu et al., "Facile synthesis of monodispersed silver nanoparticles on graphene oxide sheets with enhanced antibacterial activity," *New Journal of Chemistry* 35(7):1418-1423, 2011.
Ma et al., "Preparation, characterization and antibacterial properties of silver-modified graphene oxide," *Journal of Materials Chemistry* 21(10):3350-3352, 2011.
McAllister et al., "Single Sheet Functionalized Graphene by Oxidation and Thermal Expansion of Graphite," *Chemistry of Materials* 19(18):4396-4404, 2007.
Nakajima et al., "Mechanism of Amide Formation by Carbodiimide for Bioconjugation in Aqueous Media," *Bioconjugate Chemistry* 6(1):123-130, 1995.
Pan et al., "Water-Soluble Poly(N-isopropylacrylamide)-Graphene Sheets Synthesized via Click Chemistry for Drug Delivery," *Advanced Functional Materials* 21(14):2754-2763, 2011.
Park et al., "Chemical methods for the production of graphenes," *Nature Nanotechnology* 4(4):217-224, 2009.

Peppas et al., "Hydrogels in Biology and Medicine: From Molecular Principles to Bionanotechnology," *Advanced Materials* 18(11):1345-1360, 2006.
Qi et al., "Covalent immobilization of nisin on multi-walled carbon nanotubes: superior antimicrobial and anti-biofilm properties," *Nanoscale* 3(4):1874-1880, 2011.
Rafiee et al., "Enhanced Mechanical Properties of Nanocomposites at Low Graphene Content," *ACS Nano* 3(12):3884-3890, 2009.
Rai et al., "Silver nanoparticles as a new generation of antimicrobials," *Biotechnology Advances* 27(1):76-83, 2009.
Ruiz et al., "Graphene Oxide: A Nonspecific Enhancer of Cellular Growth," *ACS Nano* 5(10):8100-8107, 2011.
Salavagione et al., "Recent Advances in the Covalent Modification of Graphene With Polymers," *Macromolecular Rapid Communications* 32(22):1771-1789, 2011.
Santos et al., "Antimicrobial graphene polymer (PVK-GO) nanocomposite films," *Chemical Communications* 47(31):8892-8894, 2011.
Shen et al., "Facile Synthesis and Application of Ag-Chemically Converted Graphene Nanocomposite," *Nano Research* 3(5):339-349, 2010.
Sovadinova et al., "Mechanism of Polymer-Induced Hemolysis: Nanosized Pore Formation and Osmotic Lysis," *Biomacromolecules* 12(1):260-268, 2011.
Spinelli et al., "Preparation and characterization of quaternary chitosan salt: adsorption equilibrium of chromium(VI) ion," *Reactive and Functional Polymer* 61(3):347-352, 2004.
Stoller et al., "Graphene-Based Ultracapacitors," *Nano Letters* 8(10):3498-3502, 2008.
Tran et al., "Nanomaterial-Based Treatments for Medical Device-Associated Infections," *Chemphyschem* 13(10):2481-2494, 2012.
Watcharotone et al., "Graphene-Silica Composite Thin Films as Transparent Conductors," *Nano Letters* 7(7):1888-1892, 2007.
Xu et al., "Facile synthesis of silver@graphene oxide nanocomposites and their enhanced antibacterial properties," *Journal of Materials Chemistry* 21(12):4593-4597, 2011.
Yadav et al., "Mechanically Robust, Electrically Conductive Biocomposite Films Using Antimicrobial Chitosan-Functionalized Graphenes," *Particle & Particle System Characterization* 30(8):721-727, 2013.
Yang et al., "Superparamagnetic graphene oxide-$Fe_3O_4$ nanoparticles hybrid for controlled targeted drug carriers," *Journal of Materials Chemistry* 19:2710-2714, 2009.
Yang et al., "Graphene in Mice: Ultrahigh In Vivo Tumor Uptake and Efficient Photothermal Therapy," *Nano Letters* 10(9):3318-3323, 2010.
Zhang et al., "Synergistic effect of chemo-photothermal therapy using PEGylated graphene oxide," *Biomaterials* 32(33):8555-8561, 2011.
Zhang et al., "Green synthesis of graphene oxide sheets decorated by silver nanoprisms and their anti-bacterial properties," *Journal of Inorganic Biochemistry* 105(9):1181-1186, 2011.
Zhu et al., "Graphene and Graphene Oxide: Synthesis, Properties, and Applications," *Advanced Materials* 22(35):3906-3924, 2010.
Zhuang et al., "Conjugated-Polymer-Functionalized Graphene Oxide: Synthesis and Nonvolatile Rewritable Memory Effect," *Advanced Materials* 22(15):1731-1735, 2010.
Zuo et al., "Fabrication of biocompatible and mechanically reinforced graphene oxide-chitosan nanocomposite films," *Chemistry Central Journal* 7(39), 2013 (11 pages).

\* cited by examiner

FIG. 2A  FIG. 2B
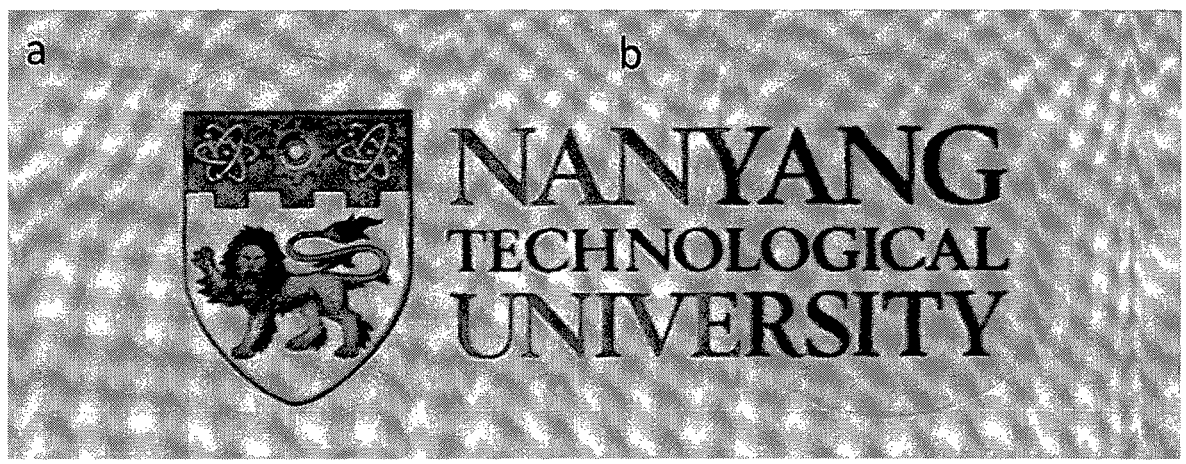
FIG. 2C  FIG. 2D
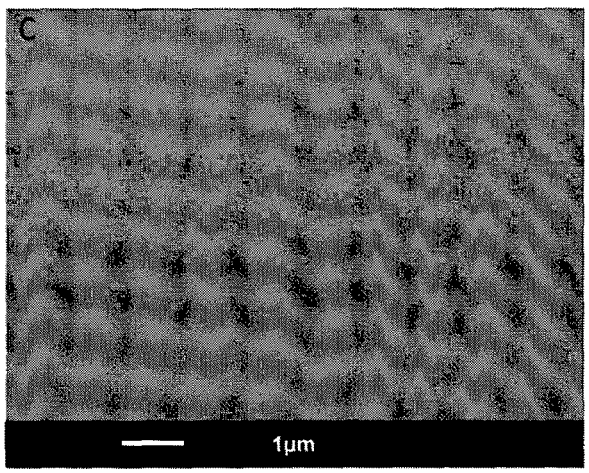 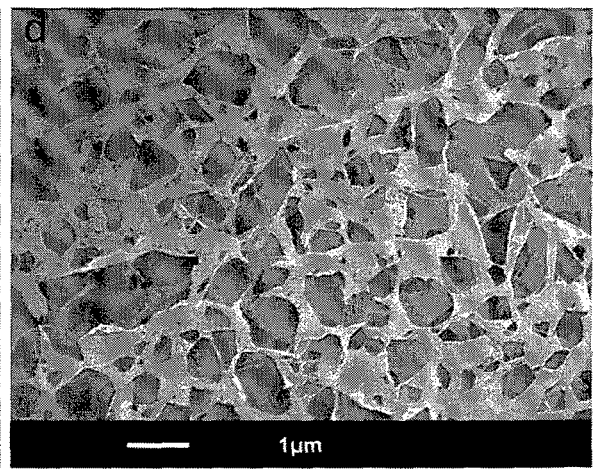

GO

GO-QC

1 μm

1 μm

HYBRID NANOMATERIAL OF GRAPHENE OXIDE NANOMATERIAL AND CATIONIC QUATERNIZED CHITOSAN

CROSS-REFERENCE TO RELATED APPLICATION

This application claims the benefit of priority of U.S. provisional application No. 61/791,784 filed on 15 Mar. 2013, the content of which is incorporated herein by reference in its entirety for all purposes.

TECHNICAL FIELD

The invention relates to a hybrid nanomaterial of graphene oxide nanomaterial that is covalently conjugated to cationic quaternized chitosan, and methods of preparation thereof. The invention also relates to antimicrobial compositions containing the hybrid nanomaterial.

BACKGROUND

Graphene refers generally to a monolayer of hexagonal sp2-bonded carbon atoms. Unique physical, chemical, electrical and mechanical properties of graphene render its usefulness in a myriad of applications, such as transparent conductive films, sensors, transistors, solar cells, capacitors, and material reinforcement.

Besides its use in electronic applications, graphene and its derivatives such as graphene oxide (GO) have been considered for use in biomedical applications, for example, nanomedicine, photo-thermal therapy, drug delivery, and bacterial inhibition. However, antimicrobial efficacy of pristine graphene and graphene oxide is poor. Even though biocidal agents such as silver nanoparticles have been incorporated into graphene/graphene oxide to improve antimicrobial potency of the graphene/graphene oxide via release of silver ions, continued release of antimicrobial reagents is toxic to mammalian cells and poses an environmental hazard in the long term.

New classes of antimicrobial agents are needed to cope with the rise of multi-drug resistant superbugs and increased regulatory pressures for safer but yet more potent disinfectants. The next generation antimicrobial agents should have high broad spectrum antimicrobial potency, good biocompatibility and low susceptibility to resistance by pathogenic microbes. Amongst existing antimicrobial agents, antibiotics which usually target specific biochemical pathways are prone to bacterial resistance. Heavy metals such as gold cannot be used in applications which forbid the presence of toxic foreign species.

There is at present no report of an effective and broad spectrum antimicrobial agent with high antimicrobial potency, low toxicity, good salt tolerance, easy retrievability and reusability. Such antimicrobial agents are needed in various applications including water treatment, environmental treatment and remediation, food processing, and preservatives.

In view of the above, there exists a need for an improved graphene-based material that may be used for biomedical applications and method of preparation thereof that overcomes or at least alleviates one or more of the above mentioned problems.

SUMMARY

In a first aspect, the invention refers to a hybrid nanomaterial consisting of graphene oxide nanomaterial covalently conjugated to cationic quaternized chitosan. The cationic quaternized chitosan is represented by formula (I)

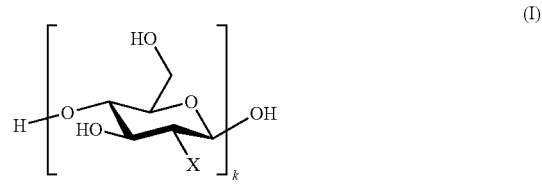

wherein each X is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$, R$^2$, R$^3$, R$^4$, and R$^5$ are independently selected from H and C$_{1-18}$ alkyl, and k is an integer from 3 to 3000.

In a second aspect, the invention refers to a method of preparing a hybrid nanomaterial consisting of graphene oxide nanomaterial covalently conjugated to cationic quaternized chitosan, wherein the cationic quaternized chitosan is represented by formula (I)

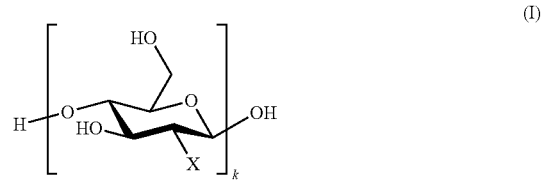

wherein each X is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$, R$^2$, R$^3$, R$^4$, and R$^5$ are independently selected from H and C$_{1-18}$ alkyl, and k is an integer from 3 to 3000, the method comprising reacting cationic quaternized chitosan of formula (I) with graphene oxide in the presence of a coupling reagent to covalently bond the cationic quaternized chitosan to the graphene oxide.

In a third aspect, the invention refers to an antimicrobial composition comprising a hybrid nanomaterial according to the first aspect or a hybrid nanomaterial prepared by a method according to the second aspect.

In a fourth aspect, the invention refers to use of an antimicrobial composition according to the third aspect to inhibit growth of microorganisms in an environment.

BRIEF DESCRIPTION OF THE DRAWINGS

The invention will be better understood with reference to the detailed description when considered in conjunction with the non-limiting examples and the accompanying drawings, in which:

FIG. 2A is a photograph of pristine glass slip.

FIG. 2B is a photograph of a transparent GO-QC (1:5) coating glass slip.

FIG. 2C is a scanning electron microscope (SEM) image of pristine glass slip. Scale bar in the figure denotes a length of 1 μm.

FIG. 2D is a SEM image of GO-QC coating glass slip. Scale bar in the figure denotes a length of 1 μm.

DETAILED DESCRIPTION

Figure 1A:
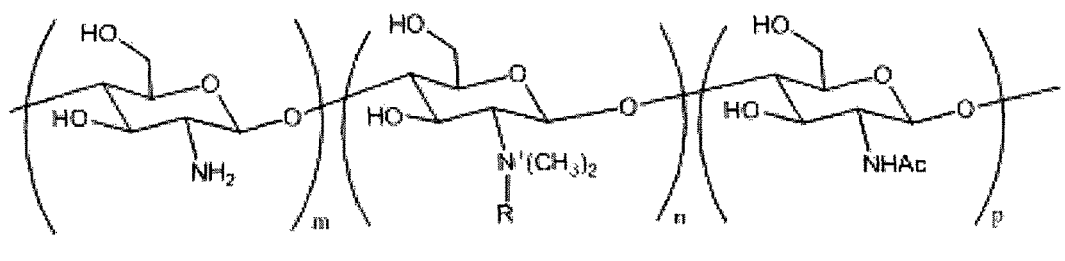
FIG. 1A shows chemical structure of quaternized chitosan (QC): dimethyldecylammonium chitosan (DMDC) according to embodiments. As shown, R may be —CH$_2$(CH$_2$)$_8$CH$_3$ or —CH$_3$. Ratio of m:n:p may be 3:5:2.

A hybrid nanomaterial which consists of graphene oxide nanomaterial covalently bonded to cationic quaternized chitosan is provided. The hybrid nanomaterial disclosed herein demonstrated a broad-spectrum antimicrobial activity for microorganisms, such as Gram-negative bacteria, Gram-positive bacteria, and fungi. The hybrid nanomaterial possesses a synergistic effect, where antimicrobial efficacy of the hybrid nanomaterial is superior to its constituent components of graphene oxide and quaternized chitosan. Further, the chitosan groups confer good biocompatibility properties on the hybrid nanomaterial as demonstrated by its reduced hemolytic activity.

With the above in mind, the present invention refers in a first aspect to a hybrid nanomaterial consisting of graphene oxide nanomaterial covalently conjugated to cationic quaternized chitosan.

The term "hybrid nanomaterial" as used herein refers to a nanoscale material formed from at least two components that are connected to one another by one or more chemical bonds, and having a functional and/or a structural property that is different from that of the individual components. Nanomaterial, otherwise termed herein as nanoscale material, refers to a material having at least one dimension that is in the nanometer range.

The hybrid nanomaterial consists of graphene oxide nanomaterial that is covalently conjugated to cationic quaternized chitosan.

The term "graphene" as used herein refers generally to a form of graphitic carbon, in which carbon atoms are covalently bonded to one another to form a two-dimensional sheet of bonded carbon atoms. The carbon atoms may be bonded to one another via sp2 bonds, and may form a 6-membered ring as a repeating unit, and may further include a 5-membered ring and/or a 7-membered ring. In its crystalline form, two or more sheets of graphene may be stacked together to form multiple stacked layers. Generally, the side ends of graphene are saturated with hydrogen atoms.

Graphene oxide (GO) refers to oxidized forms of graphene, and may include an oxygen-containing group such as a hydroxyl group, an epoxide group, a carboxyl group, and/or a ketone group. The term "graphene oxide" also includes reduced graphene oxide, which are reduced forms of graphene oxide, such as graphene oxide that has been subjected to a reduction process, thereby partially or substantially reducing it.

The graphene oxide nanomaterial is covalently conjugated to cationic quaternized chitosan, wherein the cationic quaternized chitosan is represented by formula (I)

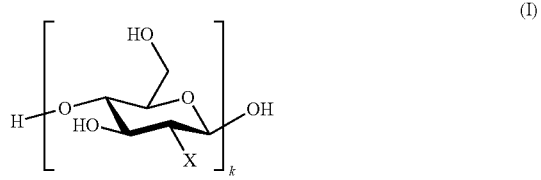

(I)

wherein each X is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$, R$^2$, R$^3$, R$^4$, and R$^5$ are independently selected from H and C$_{1-18}$ alkyl, and k is an integer from 3 to 3000.

The term "chitosan", also referred to as poly-D-glucosamine or polyglucosamine, refers to a biopolymer derived from chitin that consists of β-1,4-glykosidic linked glucosamine and, optionally, N-acetylglucosamine residues (2-acetamido-2-desoxy-β-D-glukopyranose residues), wherein the ratio of glucosamine to N-acetylglucosamine residues is greater than 1, i.e. the ratio of monomers with X=—N(R$^1$)(R$^2$) and —N$^+$(R$^3$)(R$^4$)(R$^5$) to those with X=—NH—C(O)—CH$_3$ is greater than 1.

Chitosan has good biodegradability, biocompatibility, and antimicrobial activity, which render its usefulness for biomedical applications. Quaternized chitosan, also referred to herein as quaternary ammonium chitosan, refers to a derivative of chitosan that is prepared by introducing a quaternary ammonium group on a dissociative hydroxyl group or amino group of the chitosan. As a consequence of the quaternization of the amino group, quaternized chitosan possess a permanent positive charge on the polysaccharide backbone. Due to this permanent positive charge, quaternized chitosan may also be termed as cationic quaternized chitosan.

Referring to formula (I), each X in the formula is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$, R$^2$, R$^3$, R$^4$, and R$^5$ are independently selected from H and C$_{1-18}$ alkyl, and k is an integer from 3 to 3000.

The term "C$_1$-C$_{18}$ alkyl" refers to a fully saturated aliphatic hydrocarbon having 1 to 18 carbon atoms, e.g. it means that the alkyl group comprises 1 carbon atom, 2 carbon atoms, 3 carbon atoms etc. up to and including 18 carbon atoms. The C$_1$-C$_{18}$ alkyl group may be straight chain or branched chain, and may be substituted or unsubstituted. Exemplary substituents include, but are not limited to, C$_{1-6}$ aliphatic group, hydroxy, alkoxy, cyano, halogen group, nitro, silyl, and amino, including mono- and di-substituted amino groups. Specific exemplary substituents include C$_1$-C$_{10}$ alkoxy, C$_5$-C$_{10}$ aryl, C$_5$-C$_{10}$ aryloxy, sulfhydryl, C$_5$-C$_{10}$ aryl, thio, halogen such as F, Cl, Br, I, hydroxyl, amino, sulfonyl, nitro, cyano, and carboxyl. Examples of alkyl groups may be, but are not limited to, methyl, ethyl, n-propyl, isopropyl, n-butyl, isobutyl, s-butyl, t-butyl, n-hexyl, n-heptyl, n-octyl, n-nonyl or n-decyl and the like.

Referring to formula (I), k is an integer from 3 to 3000. For example, k may be an integer from 3 to 2500, 3 to 2000, 3 to 1500, 3 to 1000, 3 to 500, 100 to 2500, 500 to 3000, 500 to 2000, 1000 to 3000, 1000 to 2000, 1500 to 3000, 2000 to 3000, or 2500 to 3000.

In various embodiments, R$^1$ and R$^2$ are selected from H and C$_{1-18}$ alkyl, preferably H; and R$^3$, R$^4$, and R$^5$ are each independently C$_{1-10}$ alkyl. In specific embodiments, R$^1$ and R$^2$ are H, and R$^3$, R$^4$, and R$^5$ are each independently C$_{1-10}$ alkyl.

In various embodiments, R$^3$ and R$^4$ are methyl and R$^5$ is C$_{1-10}$ alkyl, preferably methyl, ethyl, n-propyl, n-butyl, n-pentyl, n-hexyl, n-heptyl, n-octyl, n-nonyl or n-decyl. In specific embodiments, R$^3$ and R$^4$ are methyl and R$^5$ is selected from the group consisting of methyl, ethyl, n-propyl, n-butyl, n-pentyl, n-hexyl, n-heptyl, n-octyl, n-nonyl, and n-decyl.

The ratio of monomers with X=—N(R$^1$)(R$^2$) and X=—N$^+$(R$^3$)(R$^4$)(R$^5$) to monomers with X=—NH—C(O)—CH$_3$ may be in the range of 2:1 to 5:1, preferably about 4:1. For example, the ratio of monomers with X=—N(R$^1$)(R$^2$) and X=—N$^+$(R$^3$)(R$^4$)(R$^5$) to monomers with X=—NH—C(O)—CH$_3$ may be in the range of about 2:1 to about 4:1, about 2:1 to about 3:1, about 3:1 to about 4:1, or about 3:1 to about 5:1; about 2:1, about 3:1, about 4:1, or about 5:1. In specific embodiments, the ratio of monomers with X=—N(R$^1$)(R$^2$) and X=—N$^+$(R$^3$)(R$^4$)(R$^5$) to monomers with X=—NH—C(O)—CH$_3$ is about 4:1.

The ratio of monomers with X=—N(R$^1$)(R$^2$) to monomers with X=—N$^+$(R$^3$)(R$^4$)(R$^5$) is in the range of 1:4 to 4:1, preferably about 1:2 to 1:1. For example, the ratio of monomers with X=—N(R$^1$)(R$^2$) to monomers with X=—N$^+$(R$^3$)(R$^4$)(R$^5$) may be in the range of about 1:3 to about 4:1, about 1:2 to about 4:1, about 1:2 to about 3:1, about 1:2 to about 2:1, about 1:2 to about 1:1; about 1:2, or about 1:1. In specific embodiments, the ratio of monomers with X=—N ($R^1$)($R^2$) to monomers with X=—$N^+$($R^3$)($R^4$)($R^5$) is in the range of about 1:2 to about 1:1.

The graphene oxide nanomaterial is covalently conjugated to the cationic quaternized chitosan. The term "covalently conjugated" refers to formation of one or more covalent bonds between the graphene oxide nanomaterial and the cationic quaternized chitosan. The cationic quaternized chitosan may be covalently bonded to the graphene oxide via an amide bond.

As mentioned above, antimicrobial efficacy of the hybrid nanomaterial is superior to its constituent components of graphene oxide and quaternized chitosan. By conjugating graphene oxide with cationic quaternized chitosan, antimicrobial efficacy of pristine graphene oxide is improved. Without wishing to be bound by theory, it is postulated that cationic charge on the quaternized chitosan results in an electrostatic driven contact with the microbial cell envelope which is anionic. Attraction between the cationic hybrid nanomaterial and the anionic microbial cells promote incidence of contact or collision of the hybrid nanomaterial with the microbial cells. In so doing, sharp edges of the graphene oxide nanomaterial driven to the microbial cell envelope disrupt membrane of the microbe. The loss of membrane integrity and leakage of inner components lead to eventual cell death, and result in improved antimicrobial efficacy of the hybrid nanomaterial.

The improvement in antimicrobial efficacy may also be effected by improvements in dispersion of the hybrid nanomaterial in an aqueous environment due to modification of graphene oxide with quaternized chitosan, thereby overcoming aggregation tendencies of graphene oxide in solution. In addition, the quaternized chitosan confers good biocompatibility properties on the hybrid nanomaterial.

In one embodiment, the cationic quaternized chitosan comprises or consists essentially of dimethyldecylammonium chitosan having general formula (II)

the hybrid nanomaterial may be in the range of about 1:2 to about 1:2.8, about 1:2 to about 1:2.5, about 1:2 to about 1:2.3, about 1:2.05 to about 1:2.25, or about 1:2.05 to about 1:2.2, about 1:2.07, about 1:2.1, about 1:2.15, or about 1:2.2. In specific embodiments, the weight ratio of graphene oxide to cationic quaternized chitosan in the hybrid nanomaterial is in the range of about 1:2.05 to about 1:2.2.

In a second aspect, a method of preparing a hybrid nanomaterial consisting of graphene oxide (GO) nanomaterial covalently conjugated to cationic quaternized chitosan is provided. The cationic quaternized chitosan is represented by formula (I)

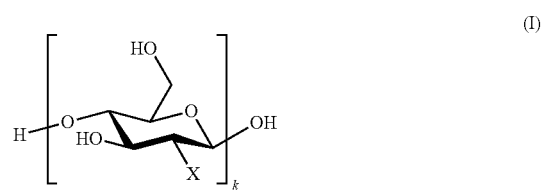

(I)

wherein each X is independently selected from —NH—C(O)—$CH_3$, —N($R^1$)($R^2$) and —$N^+$($R^3$)($R^4$)($R^5$), provided that at least one X is —$N^+$($R^3$)($R^4$)($R^5$), $R^1$, $R^2$, $R^3$, $R^4$, and $R^5$ are independently selected from H and $C_{1-18}$ alkyl, and k is an integer from 3 to 3000.

As mentioned above, $R^1$ and $R^2$ are selected from H and $C_{1-18}$ alkyl, preferably H; and $R^3$, $R^4$, and $R^5$ are each independently $C_{1-10}$ alkyl. In specific embodiments, $R^3$ and $R^4$ are methyl and $R^5$ is $C_{1-10}$ alkyl, preferably methyl, ethyl, n-propyl, n-butyl, n-pentyl, n-hexyl, n-heptyl, n-octyl, n-nonyl or n-decyl.

In various embodiments, the ratio of monomers with X=—N($R^1$)($R^2$) and X=—$N^+$($R^3$)($R^4$)($R^5$) to monomers

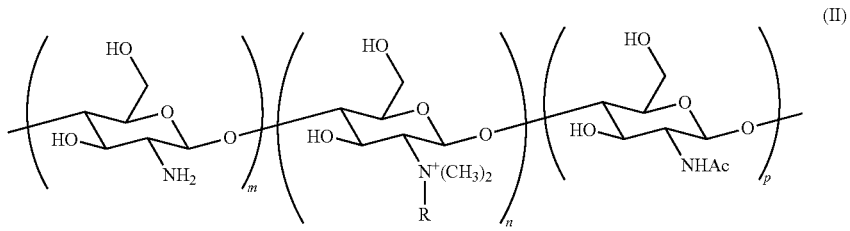

(II)

wherein R is selected from the group consisting of —$CH_2$($CH_2$)$_8$$CH_3$ and —$CH_3$; and ratio of m:n:p is 3:5:2.

The weight ratio of graphene oxide to cationic quaternized chitosan in the hybrid nanomaterial may be in the range of about 1:2 to about 1:3. For example, the weight ratio of graphene oxide to cationic quaternized chitosan in with X=—NH—C(O)—$CH_3$ is in the range of 2:1 to 5:1, preferably about 4:1. The ratio of monomers with X=—N($R^1$)($R^2$) to monomers with X=—$N^+$($R^3$)($R^4$)($R^5$) may be in the range of 1:4 to 4:1, preferably about 1:2 to 1:1.

In specific embodiments, the cationic quaternized chitosan comprises or consists essentially of dimethyldecylammonium chitosan having general formula (II)

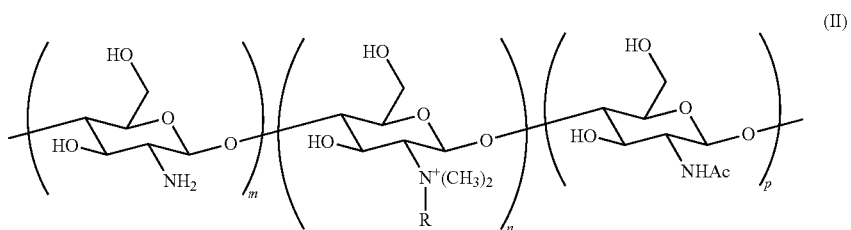

(II)

wherein R is selected from the group consisting of —CH$_2$(CH$_2$)$_8$CH$_3$ and —CH$_3$; and ratio of m:n:p is 3:5:2.

The method includes reacting cationic quaternized chitosan of formula (I) with graphene oxide in the presence of a coupling reagent to covalently bond the cationic quaternized chitosan to the graphene oxide.

The coupling reagent may be any suitable compound that is able to covalently bind the cationic quaternized chitosan to the graphene oxide nanomaterial. In various embodiments, the coupling reagent is a carbodiimide compound. The term "carbodiimide compound" as used herein refers to a water-soluble organic compound having at least one carbodiimide functional group of formula —N=C=N—. In specific embodiments, the coupling reagent comprises 1-ethyl-3-(3-dimethylaminopropyl)carbodiimide.

Any suitable amount of carbodiimide compound that allows covalently binding of the cationic quaternized chitosan to the graphene oxide nanomaterial may be used. In various embodiments, concentration of the carbodiimide compound is in the range of about 100 mM to about 2000 mM, such as about 100 mM to about 1500 mM, about 100 mM to about 1000 mM, about 100 mM to about 500 mM, about 500 mM to about 2000 mM, about 500 mM to about 1500 mM, about 500 mM to about 1000 mM, about 1000 mM to about 2000 mM, about 1000 mM to about 1500 mM, about 500 mM to about 1500 mM, or about about 1000 mM to about 1500 mM.

In embodiments where the coupling reagent comprises 1-ethyl-3-(3-dimethylaminopropyl)carbodiimide, the reaction to covalently bind cationic quaternized chitosan to the graphene oxide nanomaterial may be carried out in the presence of N-hydroxysuccinimide. Advantageously, N-hydroxysuccinimide acts as a stabilizer to stabilize active intermediates that are formed during the reaction.

In various embodiments, concentration of the N-hydroxysuccinimide is in the range of about 100 mM to about 2000 mM.

The cationic quaternized chitosan may be covalently bonded to the graphene oxide via an amide bond.

Any suitable amount of graphene oxide and cationic quaternized chitosan may be used to form the hybrid nanomaterial. In various embodiments, the weight ratio of graphene oxide to the cationic quaternized chitosan may be in the range of about 1:1 to about 1:10. For example, the weight ratio of graphene oxide to the cationic quaternized chitosan may be in the range of about 1:1 to about 1:8, about 1:1 to about 1:5, about 1:1 to about 1:3, about 1:3 to about 1:10, about 1:5 to about 1:10, or about 1:8 to about 1:10.

In a third aspect, the invention refers to an antimicrobial composition comprising a hybrid nanomaterial according to the first aspect, or a hybrid nanomaterial prepared by a method according to the second aspect.

Amount of hybrid nanomaterial in the antimicrobial composition may vary depending on the intended application. In various embodiments, concentration of the hybrid nanomaterial in the composition is in the range of about 20 μg ml$^{-1}$ to about 3000 μg ml$^{-1}$. For example, concentration of the hybrid nanomaterial in the composition may be in the range of about 20 μg ml$^{-1}$ to about 3000 μg ml$^{-1}$, about 100 μml$^{-1}$ to about 3000 μg ml$^{-1}$, about 500 μg ml$^{-1}$ to about 3000 μg ml$^{-1}$, about 1000 μg ml$^{-1}$ to about 3000 μg ml$^{-1}$, about 1500 μg ml$^{-1}$ to about 3000 μg ml$^{-1}$, or about 2000 μg ml$^{-1}$ to about 3000 μg ml$^{-1}$. In specific embodiments, concentration of the hybrid nanomaterial in the composition is in the range of about 250 μg ml$^{-1}$ to about 350 μg ml$^{-1}$.

The invention refers in a further aspect to use of an antimicrobial composition according to the third aspect to inhibit growth of microorganisms in an environment. The terms "microorganism" and "microbe" are used interchangeably herein, and refer to an organism that is unicellular or lives in a colony of cellular organisms such as bacteria, fungi, protest, or archea.

In various embodiments, the microorganisms are selected from the group consisting of gram-positive bacteria, gram-negative bacteria, fungus, and combinations thereof. The antimicrobial composition may be used in a method for the treatment or prevention of a bacterial or fungal infection or both bacterial and fungal infections in a subject or an organism.

In this context, the fungal infection can be caused by yeast or a non-yeast fungus. The fungal infection may, for example, be caused by fungi of the species *Candida albicans, Candida tropicalis, Candida (Clasvispora) lusitaniae, Candida (Pichia) guillermondii, Lodderomyces elongisporus, Debaryomyces hansenii, Pichia stipitis, Aspergillus fumigatus, Blastomyces dermatitidis, Cladophialophora bantiana, Coccidioides immitis, Cryptococcus neoformans, Fusarium* spp., *Microsporum* spp., *Penicillium marneffei* or *Trichophyton* spp.

The bacterial infection may be caused by a Gram negative or a Gram positive bacterium. The term "gram-positive bacteria" refers to bacterial cells which stain violet (positive) in the Gram stain assay. The Gram stain binds peptidoglycan which is abundant in the cell wall of gram-positive bacteria. In contrast thereto, the cell wall of "gram-negative bacteria" is low in peptidoglycan, thus gram-negative bacteria adopt the counterstain in the gram stain assay. The bacterial infection may, for example, be caused by bacteria of the genus *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Veillonella, Vibrio* or *Yersinia*. In specific embodiments, the infection is caused by *Staphylococcus aureus, Mycobacterium smegmatis, Pseudomonas aeruginosa, Burkholderia cepacia, Klebsiella pneumonia, Aeromonas hydrophila, Erwinia carotovora, Erwinia chrysanthemi*, or *Escherichia coli*.

In specific embodiments, the microorganisms comprise or consist of gram-negative bacteria, gram-positive bacteria, or combinations thereof. As mentioned above, cationic charge on the quaternized chitosan of the hybrid nanomaterial results in an electrostatic driven contact with the microbial cell envelope which is anionic. In so doing, sharp edges of the graphene oxide nanomaterial driven to the microbial cell envelope further disrupt membrane of the microbe. The loss of membrane integrity and leakage of inner components leads to eventual cell death, and results in improved antimicrobial efficacy of the hybrid nanomaterial.

Difference in susceptibility to graphene oxide may be explained by differences in cell wall structures between the microbes. The antimicrobial efficacy is better for gram-negative bacteria and gram-positive bacteria, as opposed to fungi, since the bacteria cells have an outer membrane and a cytoplastic membrane (gram-negative bacteria such as *E. coli*) or a cytoplasmic membrane that is protected by a layer of peptidoglycan (gram-positive bacteria such as *S. aureus*), that makes them more susceptible to attack and disruption from the sharp edge of the graphene oxide nanomaterial. The cytoplasmic membrane of fungi, such as *C. albicans*, on the other hand, is surrounded by a thick carbohydrate cell wall which is likely to confer more protection to the cell from physical stress of the graphene oxide nanomaterial, thus explaining its low susceptibility to the graphene oxide-cationic quaternized chitosan hybrid nanomaterial.

In specific embodiments, the microorganisms are selected from the group consisting of *Escherichia coli, Staphylococcus aureus, Candida albicans*, and combinations thereof.

The subject affected by the bacterial and/or fungal infection may be a mammal, such as a human being. Advantageously, it has been demonstrated that the hybrid nanomaterial has ability to retain antimicrobial activity in the presence of salt, which renders it suitable for use in ionic physiological environments. Without wishing to be bound by theory, it is postulated that the hybrid nanomaterial does not aggregate in the presence of salt due to presence of water-soluble quaternized chitosan side chains, thereby stabilizing the hybrid nanomaterials. This stability is important for retaining of antimicrobial activity of the hybrid nanomaterial.

Another advantageous feature of the hybrid nanomaterial disclosed herein relates to its reusable nature. It has been demonstrated herein that the hybrid nanomaterial is able to exert biocidal effect repeatedly, as it is prevented from absorption by the microbes. By subsequent separation of the hybrid nanomaterial from the microbes by, for example, centrifuging a sample solution containing the antimicrobial composition and bacteria cells, the hybrid nanomaterial separates from the microbes and remains suspended in solution. Since the hybrid nanomaterial is not absorbed by the microbes, it does not precipitate together with the bacteria cells, and is able to retain its antimicrobial efficacy after repeated use.

The antimicrobial composition disclosed herein may be used for all kinds of environment such as surfaces in private and public areas, where it is beneficial to interfere Gram-negative or Gram-positive bacteria and/or fungus, in order to prevent and/or treat colonization.

The antimicrobial composition may be used to inhibit growth of microorganisms in an environment alone or together with other materials such as conventional surfactants, preferably sodium dodecyl sulfate, or detergents, biocides, fungicides, antibiotics, pH regulators, perfumes, dyes or colorants.

The antimicrobial composition may be used as antibacterial agent for topical use in cleaning and treatment solutions such as disinfectants, detergents, household cleaner and washing powder formulations in the form of a spray or a dispensable liquid. For example, the antimicrobial composition may be applied to windows, floors, clothes, kitchen and bathroom surfaces and other surfaces in the area of food preparation and personal hygiene.

The antimicrobial composition may also be used as antibacterial ingredients in personal hygiene articles, toiletries and cosmetics. Examples of such toiletries include oral hygiene products, which refer to any composition which is used in the mouth in order to promote oral hygiene. These compositions may be in the form of aqueous solutions, for example, a mouth wash composition; or gels, for example toothpaste or dentrifice compositions. In this context, a dentrice refers to a paste, liquid or powder used to help maintain acceptable oral hygiene. Exemplary personal hygiene articles include but are not limited to soaps, shampoos, shower gels, ointments, creams, lotions, deodorants and disinfectants and storage solutions for contact lenses. Examples of cosmetics include, but are not limited to, foundation make-up, eye liner, lip stick, and lip gloss.

The antimicrobial composition may also be used in industrial settings such as ship hulls, paper manufacturing, oil recovery and food processing. The compounds may also be applied to water processing plants or water distribution systems, such as water pipes, water injection jets, heat exchangers and cooling towers.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art.

As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

According to embodiments, a nanomaterial-polymer conjugation based on graphene oxide functionalized with one kind of quarternized chitosan (QC), specifically dimethyldecylammonium chitosan (DMDC) has been prepared to improve its antimicrobial properties. In various embodiments, QC molecules were covalently grafted onto GO nanosheets by a facile single-step coupling reaction between carboxyl and amine groups using 1-ethyl-3-(3-dimethylaminopropyl)carbodiimide (EDC) and N-hydroxysuccinimide (NHS).

The GO-QC nanosheet shows broad-spectrum antimicrobial activity for Gram-negative and Gram-positive bacteria, and fungi. The antimicrobial activities of pristine GO, QC, and GO-QC were investigated for three microbes: Gram-negative bacterium *Escherichia Coli* (*E. coli*, ATCC8739), Gram-positive bacterium *Staphylococcus aureus* (*S. aureus*, ATCC6538), and fungus *Candida. albicans* (*C. albicans*, ATCC10231). The GO-QC shows broad-spectrum antimicrobial activity against these pathogens and even lower minimum bactericidal concentration (MBC) of 5-30 μg/mL than the QC polymer itself (16-60 μg/mL) or GO alone (greater than 5000 μg/mL), thus demonstrating that antimicrobial efficacy of GO-QC is superior to GO or QC individually.

FESEM analysis shows that GO-QC induces more significant microbial cell wall/membrane damage than GO and QC, where obvious holes can be observed with GO-QC treated cells. QC appeared to have only a membrane-wrinkling effect while GO incurred only relatively minor morphology changes. Values of percentage (%) kill of microbe in the presence of salts (such as NaCl up to 150 mM) were also evaluated. Scanning electron microscopy (SEM) and adenosine triphosphate (ATP) leakage tests showed that the microbe cell envelopes were damaged. The reusability of GO-QC was also demonstrated. The difference in the interaction of the QC polymer and the nanohybrid with bacteria was demonstrated by fluorescence dye staining of these agents.

The synergistic combination of GO and QC confers the GO-QC nanosheet unique properties: it comprises a condensed carrier of quaterinzed chitosan, where the cationic charge of the QC groups is responsible for electrostatic-driven contact with the anionic microbial cell envelope and the sharp edges of the single atom layer nanosheet would further enhance membrane disruption. Importantly, the chitosan groups confer the GO-QC nanosheet good biocompatibility properties, as demonstrated by the reduced hemolytic activity of the GO nanosheet. Such covalently functionalized GO-polymer hybrid material with improved antimicrobial activity has not been reported to date.

Example 1

GO-QC Nanoplatelets Preparation

A GO-graft-cationic polymer nanosuspension based on GO grafted with quaternized chitosan (QC), specifically dimethyldecylammonium chitosan (DMDC) was prepared.

Example 1.1

Preparation of Quaternized Chitosan (QC)

Figure 4:
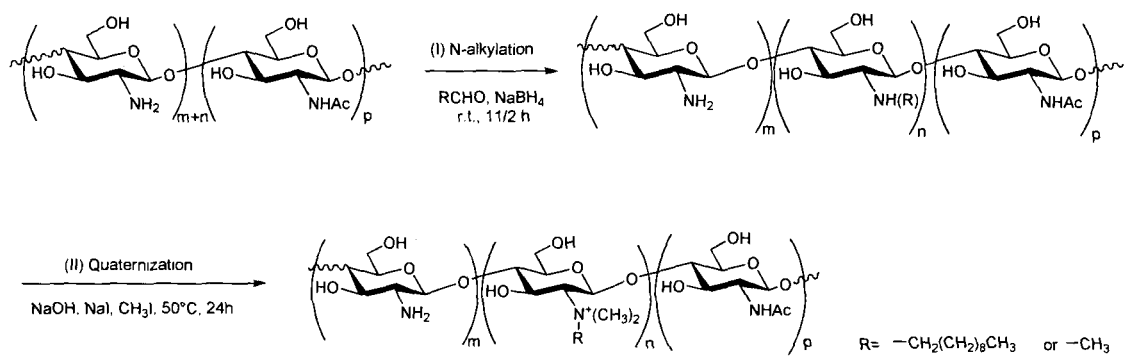
FIG. 4 is a synthesis schematic of quaternized chitosan (dimethyldecylammonium-chitosan). Condition (I): N-alkylation carried out using RCHO, in presence of $NaBH_4$ at room temperature for 1.5 hours. Condition (II): Quaternization using NaOH, NaI, and $CH_3I$, at 50° C. for 24 hours.

FIG. 4 is a synthesis schematic of quaternized chitosan (dimethyldecylammonium-chitosan).

Chitosan (1 g, 6.2 mmol) was first pre-dissolved in acetic acid (1%, 100 ml), then decanal (0.97 g, 6.2 mmol) was added and stirred for 1 h at room temperature. After this, the pH was increased to 4.5 followed by addition of sodium borohydride (9.3 mmol) and further stirring of the mixture for 1.5 h. The pH was then further increased to 10 by adding sodium hydroxide (NaOH) solution (1 M). The white precipitates that formed were filtered and washed with distilled water until neutrality. Soxhlet extraction using ethanol and diethyl ether mixture was performed to remove unreacted reagents. The resulting N-decyl chitosan (1 g, 6.2 mmol) was then added to N-methylpyrrolidone (NMP) (50 ml) and NaOH solution (1.5 M, 15 ml). After 30 min of stirring at 50° C., methylation was performed as follows: sodium iodide (1.08 g, 7.2 mmol) and methyl iodide (11.2 g, 78.7 mmol) were added to the chitosan/NMP/NaOH mixture and then reacted under stirring for 24 h at 50° C. The solution was then suction filtered. After dropping the filtrate into acetone (400 ml), the precipitate obtained was filtered and then dried under vacuum to yield the product.

Example 1.2

Preparation of GO Nanoflakes

Figure 1B:
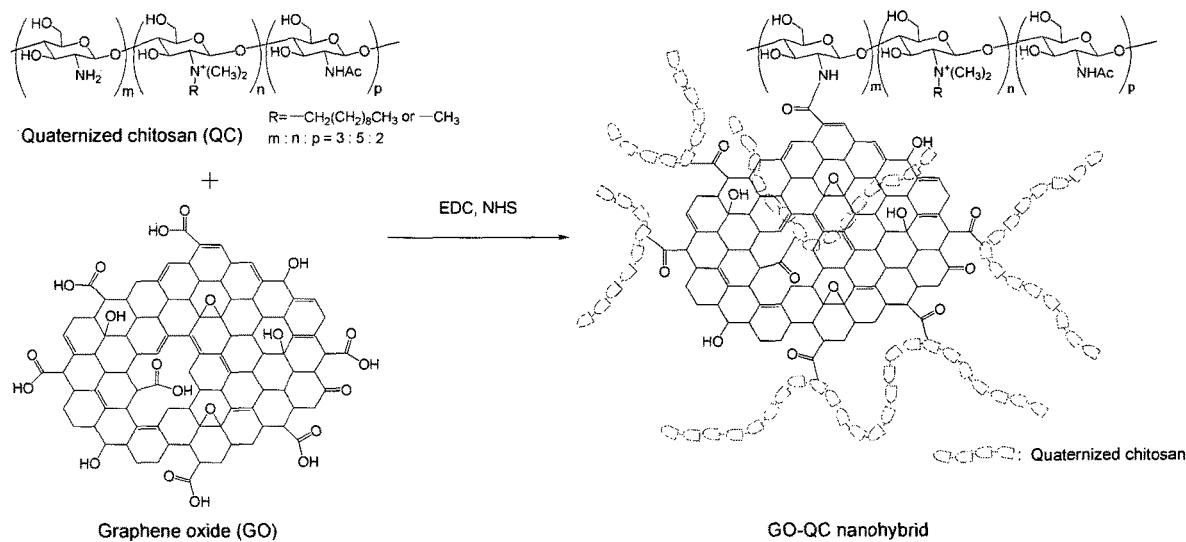
FIG. 1B depicts a chemical reaction for synthesis of graphene oxide-quaternized chitosan (GO-QC) nanohybrid by amine coupling reaction in the presence of 1-Ethyl-3-(3-dimethylaminopropyl)carbodiimide (EDC) and N-Hydroxysuccinimide (NHS). As shown in the figure, QC having structure depicted in FIG. 1A is reacted with GO in the presence of EDC and NHS to form GO-QC nanohybrid.

GO nanoflakes prepared by exfoliation of, oxidized graphite contain abundant oxidized functional groups such as carboxyl, carbonyl, phenol hydroxyl, and epoxide groups (FIG. 1B). The carboxyl groups on GO may be activated by carbodiimide, and react with primary amine groups to result in amide bond formation.

Figure 6A:
FIG. 6A is a Field Emission Scanning Electron Microscope (FESEM) image of GO and GO-QC (1:5). Scale bar in the figures denote a length of 1 μm.
Figure 6A:
Figure 6B:
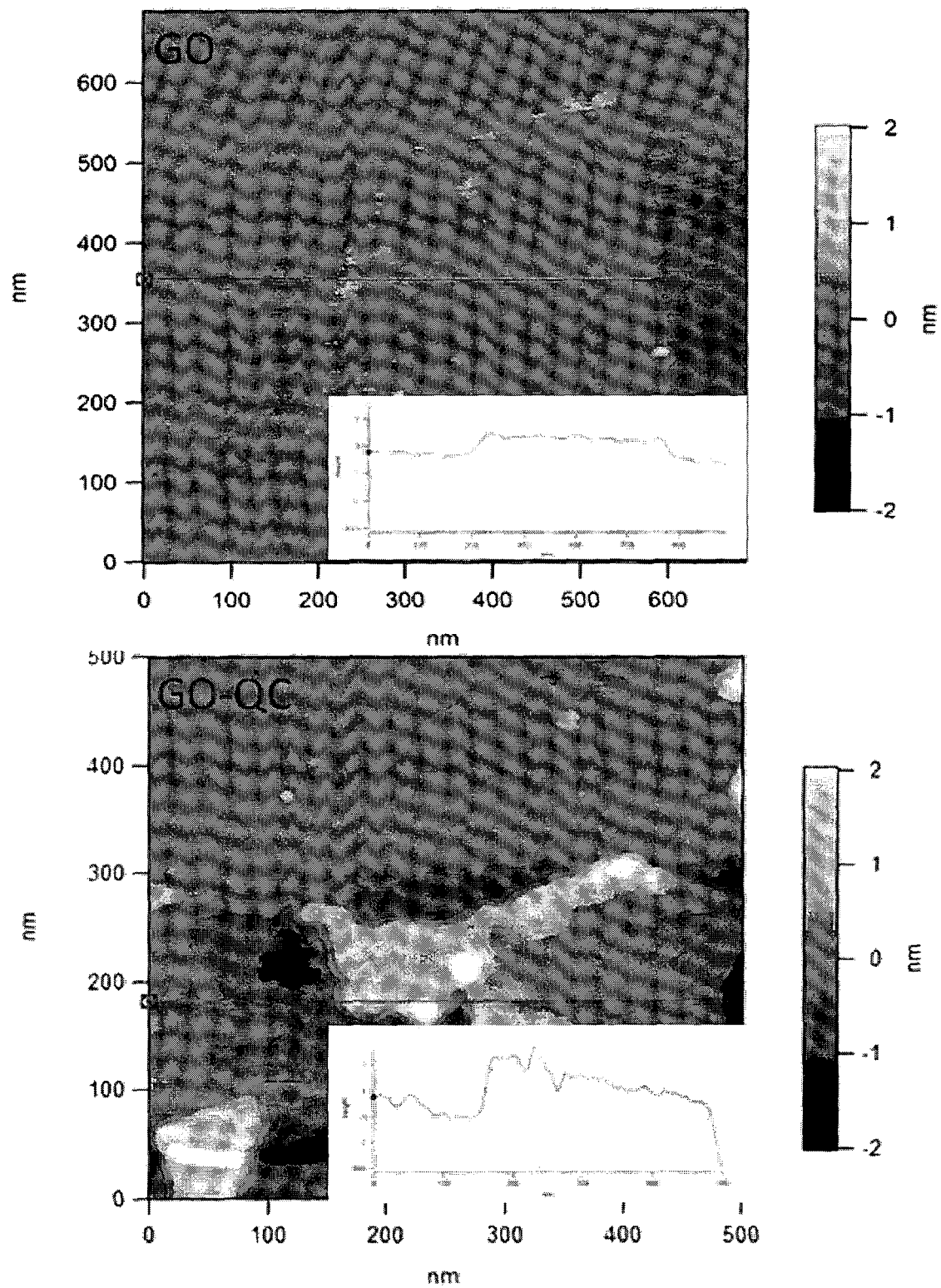
FIG. 6B is an atomic force microscopy (AFM) image of GO and GO-QC (1:5) with the thickness determination.

Briefly, GO nanoflakes were chemically exfoliated from natural graphite powder by a modified Hummers method which introduces abundant oxidized functional groups such as carboxyl groups to the GO nanoflakes. The GO nanoflakes have an average thickness of about 1 nm and average diameter of 746±308 nm (FIG. 6A, 6B and FIG. 7).

After reaction, the suspension was centrifuged (20000×g, 2 h) to remove the unreacted GO nanoflakes, then filtered with polyamide membrane (0.2 μm, Sartorius) and thoroughly washed using deionized water to remove the unreacted reagents. The solid residue was dispersed in water, dialyzed using a cellulose membrane (Sigma, MWCO 14000) for 3 days and then freeze dried. The synthesized GO-QC was characterized by Fourier transform infrared spectrum (FTIR, Nicolet 5700) and thermogavimetric analysis (TGA, Netzsch STA 409).

Example 1.3

Preparation and Characterization of GO-QC Nanoflakes

A series of GO-QC derivatives with weight ratio of GO to QC varying from 1:1 to 1:10 (w/w) was synthesized.

Figure 5:
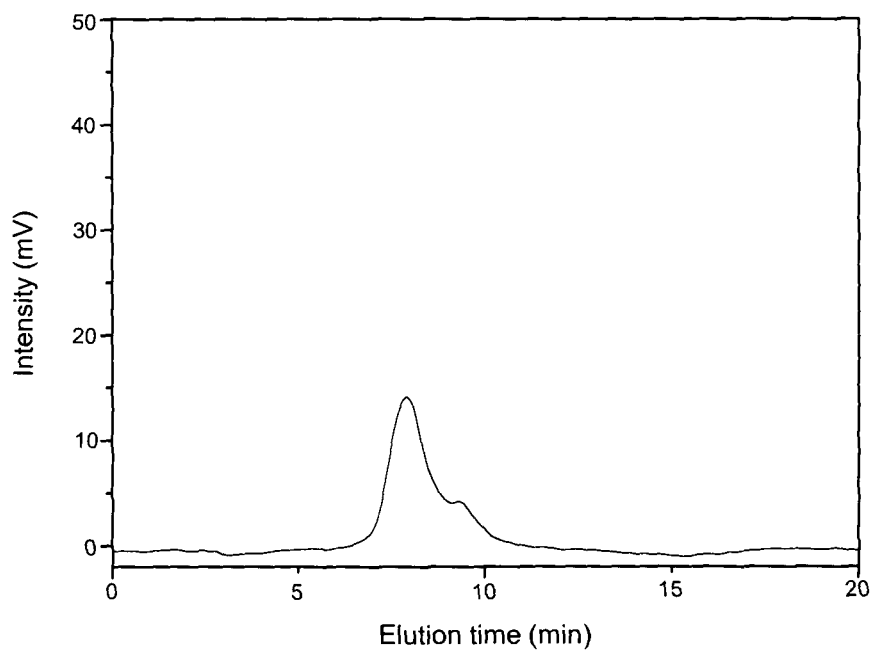
FIG. 5 is a graph showing gel permeation chromatography (GPC) spectrum of synthesized quaternized chitosan (dimethyldecylammonium-chitosan). Y-axis: intensity (mV); x-axis: elution time (minutes).

QC molecules were covalently grafted onto GO nanoflakes by a coupling reaction between carboxyl and amine groups, using 1-ethyl-3-(3-dimethylaminopropyl)carbodiimide hydrochloride (EDC, Sigma) and N-hydroxysuccinimide (NHS) (FIG. 1A and FIG. 1B). The synthesized. QC (FIG. 4) has a quaternization degree of 56% and molecular weight of 38 kDa (FIG. 5).

The quaternization degree of the chitosan derivative was estimated from elemental analysis and calculated from the relation:

Quaternization degree =

$$\frac{\frac{C}{N} \text{ mol \%(chitosan derivative)} - \frac{C}{N} \text{ mol \%(chitosan)}}{\frac{C}{N} \text{ mol \%(chitosan)}} \times 100\%$$

FIG. 6A and FIG. 7 show that both the GO and GO-QC hybrids are individual nanoflakes. AFM imaging of the GO-QC (1:5) (FIG. 6B) indicates that the average thickness has increased to about 2 nm whilst the average diameter of the GO-QC(1:5) hybrid is not much changed (573±160 nm).

Figure 6C:
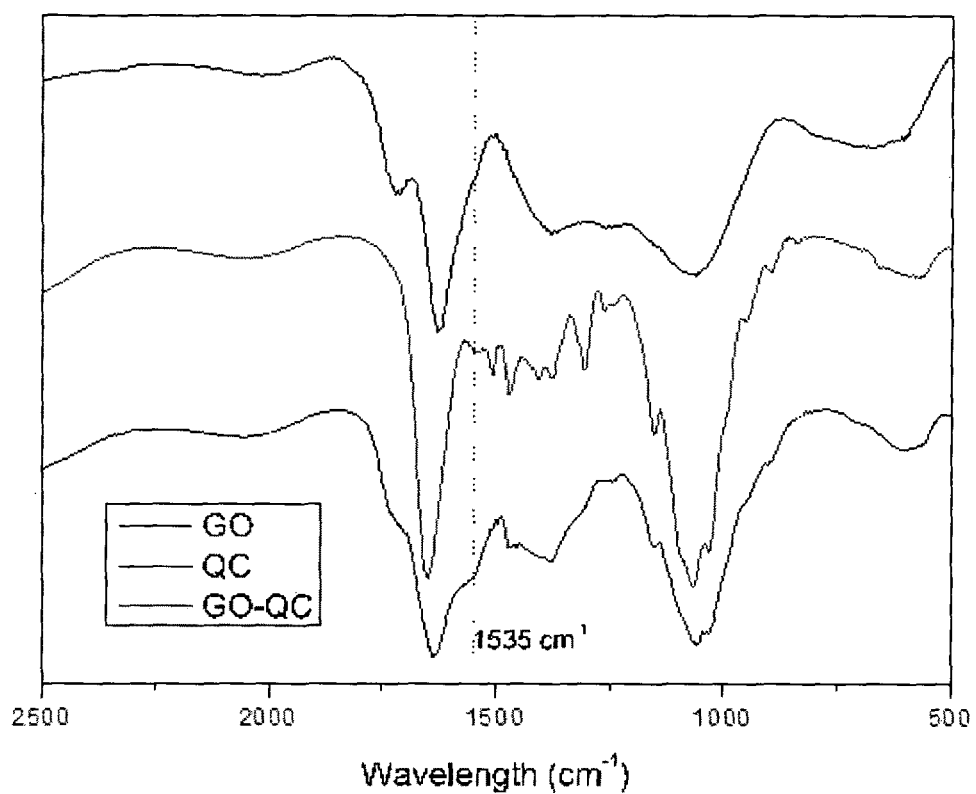
FIG. 6C is a graph showing Fourier transform infrared spectroscopy (FTIR) spectra of GO, QC and GO-QC (1:5).

FIG. 6C shows the FITR spectra of pristine GO, QC and a typical GO-QC (1:5). The peak at 1535 cm$^{-1}$ in the GO-QC spectrum, which is absent in the GO spectrum, corresponds to the newly formed —NHCO— bond between GO and QC, corroborating that QC molecules have been grafted onto the GO through an amide linkage. In the spectrum of QC, there is also a weak peak at 1535 cm$^{-1}$ which is due the incomplete deacetylation of chitosan.

Figure 6D:
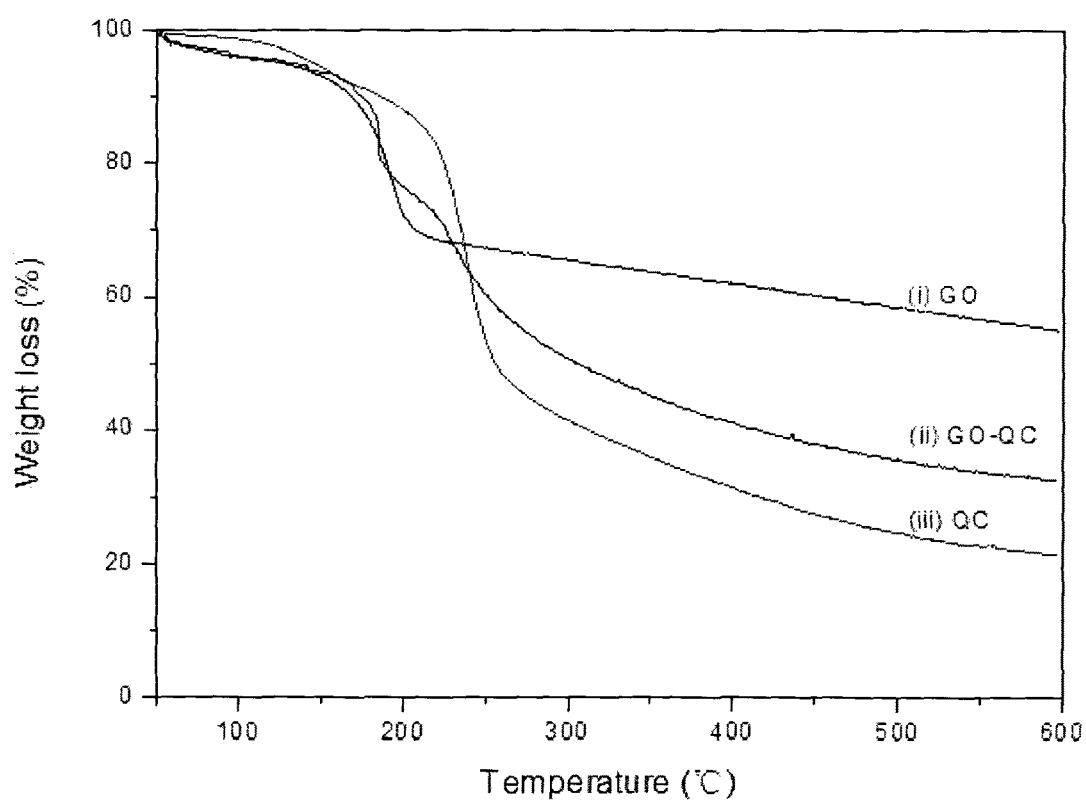
FIG. 6D is a graph showing thermogravimetric analysis (TGA) curves of (i) GO, (ii) GO-QC (1:5) and (iii) QC at a heating rate of 10° C. per min under nitrogen protection. Y-axis: weight loss (%); x-axis: temperature (° C.).
Figure 7A:
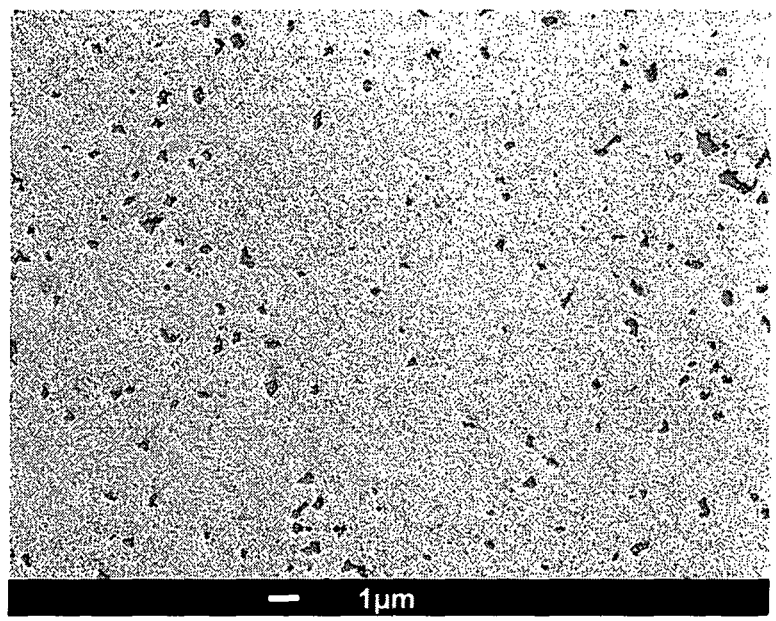
FIG. 7A is a SEM image showing GO. Scale bar in the figure denotes a length of 1 μm.
Figure 7B:
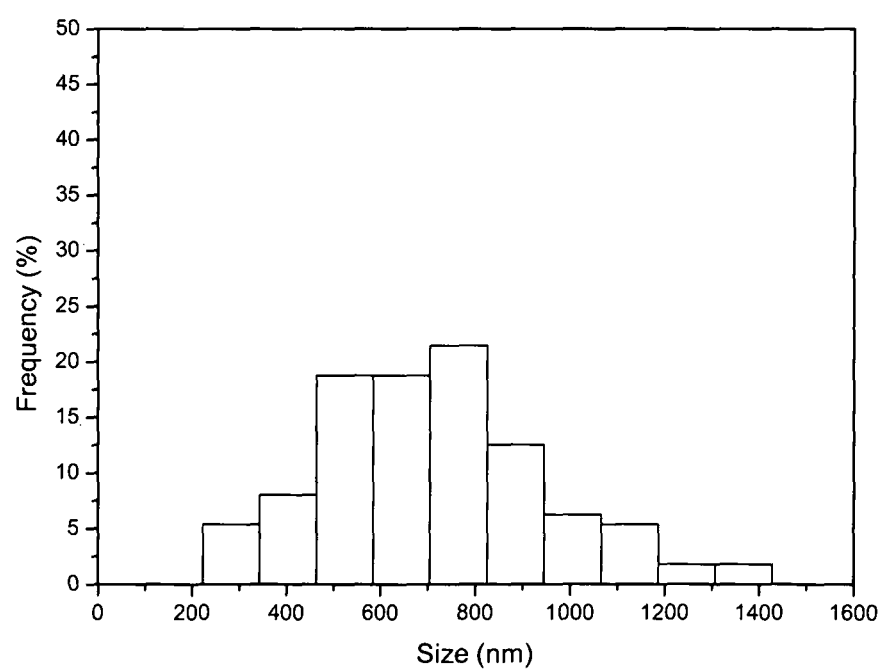
FIG. 7B is a graph showing size distribution of GO. At least 100 nanoflakes were measured for each sample to obtain the average size and distribution. Y-axis: Frequency (%); x-axis: size (nm).
Figure 7C:
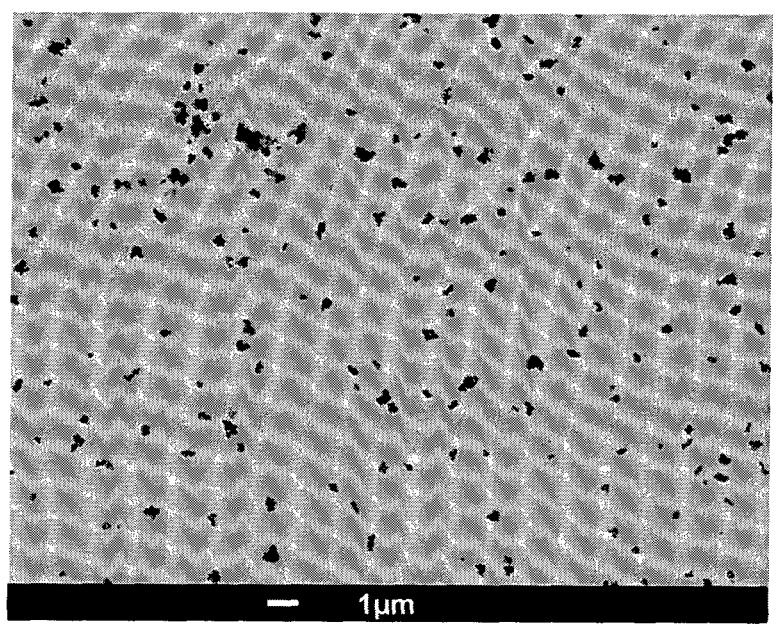
FIG. 7C is a SEM image showing GO-QC (1:5). Scale bar in the figure denotes a length of 1 μm.
Figure 7D:
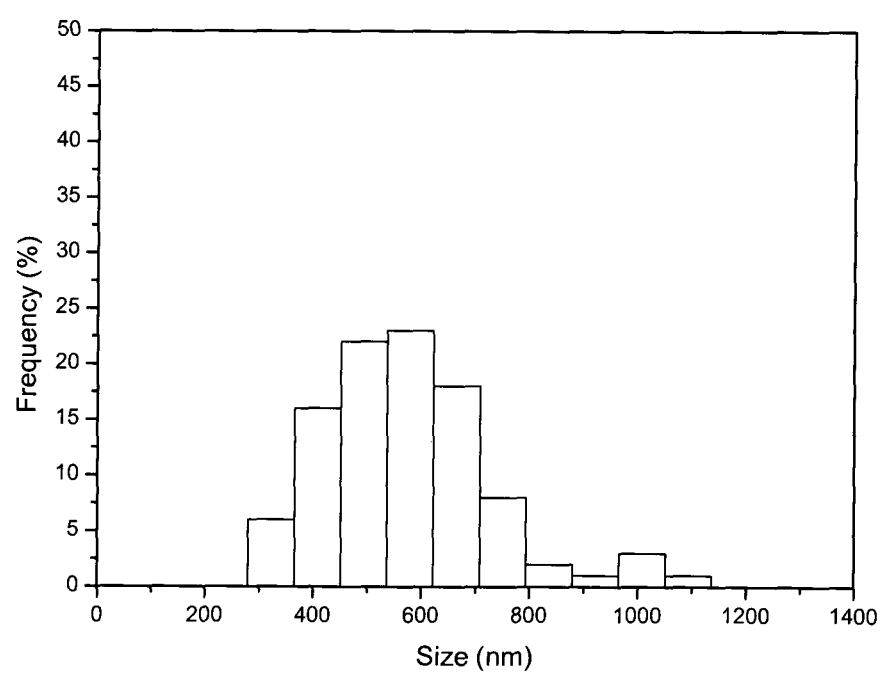
FIG. 7D is a graph showing size distribution of GO-QC (1:5). At least 100 nanoflakes were measured for each sample to obtain the average size and distribution. Y-axis: Frequency (%); x-axis: size (nm).

TGA analysis was carried out between 50 to 600° C. at a heating rate of 10° C. min$^{-1}$ under protection of nitrogen (FIG. 6D).

GO lost 4% of its weight below 100° C., which is due to the evaporation of absorbed water in its π-stacked structure. The major weight loss of GO was observed between 165° C. to 215° C., which is likely due to pyrolysis of liable oxygen-containing groups.

In contrast, QC has less than 2% weight loss below 100° C., but 35% weight loss between 210° C. to 250° C., which is due to the cleavage of substituent groups and decomposition of glucopyranose rings.

The weight loss curve of GO-QC has two stages which can be attributed to the major losses of GO (165° C. to 195° C.) and QC (210° C. to 250° C.) respectively. From the weight losses in these two main regimes, the actual weight ratios of GO to QC may be inferred and these values differ from the design values (Table 1).

For the designed GO:QC reactant weight ratios of 1:1 to 1:5, the measured GO:QC ratios were respectively 1:0.54 to 1:2.07 instead, indicating that around 50% of QC molecules was successfully grafted onto GO nanoflakes. However, with the designed GO:QC weight ratio of 1:10, the measured GO:QC ratio determined by TGA was 1:2.20, indicating that only 22% of QC was grafted onto GO nanoflake. It appears that the measured GO:QC ratio plateaus at around the design ratio of 1:5. This may be attributed to the limited availability of carboxyl groups on GO nanoflake. The consumption of carboxyl groups on GO to near zero values was confirmed by acid titration, as follows.

Example 2

Determination of the Content of Carboxylic Acid Groups of GO and GO-QC

Content of carboxylic acid groups of GO and GO-QC was determined by an acid-base titration method. 50 mg GO or GO-QC was mixed with 10 ml NaOH solution (0.1 M) under sonication for 30 min, then stirred for 2 days. The mixture was then placed into the dialysis tube (Sigma, MWCO 14000), and dialyzed until the pH of dialysate is neutral. The combined dialysate was condensed using a rotary evaporator and titrated with 0.1 M HCl to neutral (pH=7.00). The amount of carboxylic acid groups was estimated by the amount of NaOH consumed by GO or GO-QC.

The determined content of carboxylic acid groups on pristine GO is about 5.1 mmol/g, for GO-QC (1:5) and (1:10) the content is 0.6 mmol/g and 0.5 mmol/g respectively. The small amounts carboxylic acid groups left on GO-QC nanohybrids may be masked by the grafted QC molecules, thus prevent more grafting reaction.

Example 3

Minimum Bactericidal Concentration (MBC) Determination

The minimum bactericidal concentration (MBC) of GO, QC and GO-QC was determined using a nutrient-free protocol to eliminate replication of bacteria. A two-fold dilution series of 100 μl antimicrobial reagent solution was made in 96-well microplate, followed by the addition of 100 μl bacterial/fungal suspensions at a concentration of 10$^6$ CFU ml$^{-1}$. The plates were incubated at 37° C. (28° C. for fungi) for 6 h. After incubation the sample treated bacterial/fungal suspensions were plated using MH/YM agar. MBC was

TABLE 1

Minimum bactericidal concentrations (MBC) and hemolytic activities.

| No. | Materials | A<br>GO:QC ratio determined by TGA | B<br>MBC (μg ml$^{-1}$)/Selectivity* | | | C<br>HC$_{50}$ (μg ml$^{-1}$) |
|---|---|---|---|---|---|---|
| | | | E. coli | S. aureus | C. albicans | |
| 1 | QC (DMDC) | — | 60/250 | 30/500 | 16/938 | 15000 |
| 2 | GO | — | >5000/<0.4 | >5000/<0.4 | >5000/<0.4 | 1250 |
| 3a | GO-QC (1:1)† | 1:0.54 | 310/8 | 160/16 | 160/16 | 2500 |
| 3b | GO-QC (1:2.5) | 1:1.04 | 80/63 | 40/125 | 20/250 | 5000 |
| 3c | GO-QC (1:5) | 1:2.07 | 30/333 | 10/1000 | 5/2000 | 10000 |
| 3d | GO-QC (1:10) | 1:2.20 | 30/333 | 10/1000 | 5/2000 | 10000 |

†Design ratios.
*Selectivity = HC$_{50}$/MBC determined as the lowest concentration that no bacterium/ fungus growth on the nutrition plates. The test was independently repeated twice.

Example 4

Microbe Morphology Study

The morphology changes of microorganisms induced by QC, GO and GO-QC were examined with Field Emission Scanning Electron Microscopy (FESEM, JEOL JSM-6701F).

Microbe cells were incubated with QC, GO and GO-QC at 100 µg ml$^{-1}$ for 1 h. The microbes were collected by centrifugation (1000×g, 10 min) after incubation, and then fixed with 2.5% glutaraldehyde for 4 h, followed by fixing with 1% osmium tetroxide solution for 4 h at 4° C. The sample was then dehydrated in a graded ethanol series from 20% to 100% each for 15 min, the samples were dried under a nitrogen flow. After the samples were vaccum dried and coated with platinum, they were observed with FESEM for microbe morphology changes.

Example 5

ATP Leakage Assay

The membrane disruption activity was also observed by adenosine triphosphate (ATP) leakage assay. ATP released from the bacterial cells was determined with BacTiter-Glo microbial cell viability assay kit (Promega, US) and luminometer (GloMax 20/20, Promega, US).

Briefly, mid-log phase *E. coli* was harvested by centrifugation (1000×g, 10 min) and washed with phosphate buffered saline (PBS) for three times. The bacterial suspension was diluted to 1-1.5×10$^6$ CFU ml$^{-1}$ in PBS, and the antimicrobial reagent was added with a final concentration at 100 µg ml$^{-1}$. At desired time points, 50 µl samples were collected and the released ATP concentration was determined with BacTiter-Glo kit and luminometer.

Example 6

Zeta Potential Measurement

The charge states of GO, QC and GO-QC at the concentration of 100 µg ml$^{-1}$ in water were determined with a zeta potential analyzer (ZetaPALS, Brookhaven Instruments Corporation, US).

Example 7

Antimicrobial and Hemolysis Evaluations

Three clinically significant microbes, i.e. *E. coli* (Gram-negative bacterium), *S. aureus* (Gram-positive bacterium), and *C. albicans* (fungus) were chosen as model pathogens to investigate the antimicrobial activity of GO and GO-QC.

The bacteria and fungi strains *Escherichia coli* (ATCC8739), *Staphylococcus aureus* (ATCC6538), *Candida albicans* (ATCC10231) used were obtained from American Type Culture Collection. All broths or agar media were purchased from Becton Dickinson Company (Franklin Lakes, US).

For bacteria, a single colony was inoculated in Luria-Bertani (LB) broth and cultured at 37° C. overnight, shaking at 200 rpm. Bacteria was harvested at the mid-logarithmic phase, centrifuged at 1,000×g for 10 min, and washed with phosphate buffer saline (PBS) solution to remove the residual nutrition. Fungi was inoculated in Yeast-Malt (YM) broth and cultured at 28° C. for 2 days, harvested, centrifuged and washed in the same ways as the bacteria cells.

Bacteria or fungi cells were centrifuged and the pellet was re-suspended in water and diluted to the desired concentration. 10$^8$ CFU cells were inoculated into 1 ml GO/GO-QC dispersions, then incubated at 37° C. (28° C. for fungi) under shaking conditions at 200 rpm for a desired time. The cell numbers were determined by the plate colony counting method. Briefly, 100 µl of 10-fold were pipetted into a 10 cm culture plate and spread with 50° C. LB agar (YM agar for fungi). The plates were incubated at 37° C. (28° C. for fungi) overnight (18-36 h) for colony formation. The number of colonies was counted and percentage kill determined using Equation below. This experiment was performed in triplicates.

$$\% \text{ kill} = \frac{\text{Cell count of control} - \text{Survivor count on sample}}{\text{Cell count of control}} \times 100\%$$

Firstly, the microbes were inoculated into the GO/QC/GO-QC dispersions (100 µg ml$^{-1}$) at a concentration of 10$^8$ CFU ml$^{-1}$, and the plate colony counting was performed after 1 h incubation.

The % kill of pristine GO for *E. coli*, *S. aureus* and *C. albicans* was 24.8±3.7%, 34.9±4.5% and 18.6±2.2%, respectively (FIG. 8), indicating that GO has poor bacteria and fungi killing efficacy. The QC derivative itself has excellent antimicrobial activities towards both bacteria and fungi and the respective % kills for these three microbes are 97.5±2.1%, 96.9±2.5% and 98.8±1.2%. With the GO-QC nanohybrids, dramatically higher antimicrobial activities against the three model pathogens compared to pristine GO (FIG. 8) were observed for the two higher QC contents.

With GO-QC (1:5), the respective % kills are 93.6±4.2%, 97.8±1.8% and 99.3±0.4% for three microbes respectively, which are statistically similar to those of QC itself (p>0.05, no significant difference). For GO-QC (1:10), the corresponding % kills are 93.7±1.9%, 98.4±1.5% and 98.2±1.7% which are similar with those of GO-QC (1:5) (p>0.05, no significant difference).

It appears that the antimicrobial activities plateaued beyond GO-QC (1:5), corroborating the plateauing of the measured GO:QC ratios by TGA (Table 1). The % kill value of the GO-QC hybrid appear to closely mimic that of QC but is significantly higher than those of GO.

Figure 9:
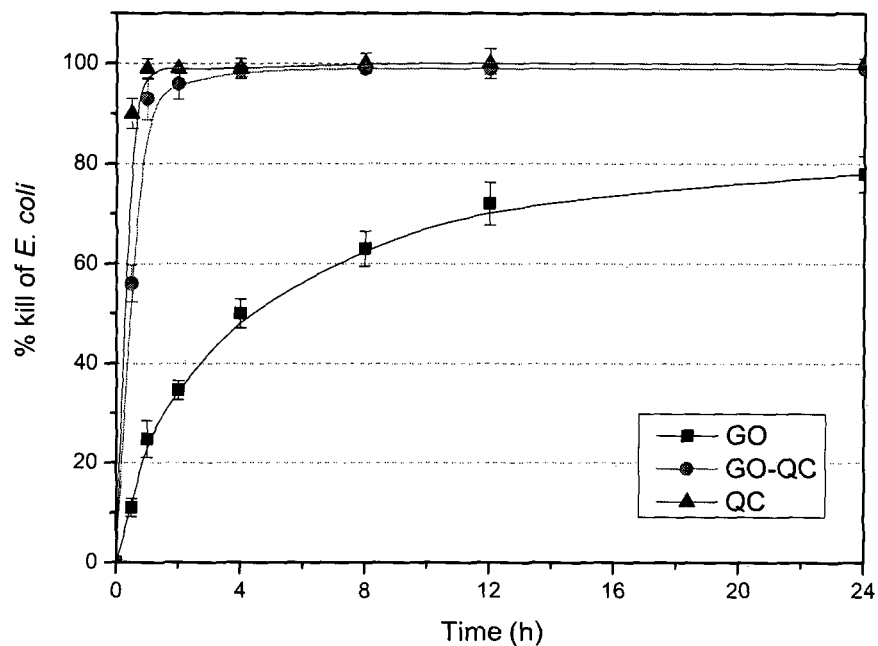
FIG. 9 is a graph showing time dependence of antimicrobial activity (killing curve) investigated by varying the incubation time of E. coli with GO, QC or GO-QC (1:5) dispersions (100 μg $ml^{-1}$) from 0.5 hour to 24 hour. The % kill of E. coli by GO, QC and GO-QC increased monotonically with incubation time. QC and GO-QC (1:5) produced high % kill quickly and reached nearly 100% after 4 h. The % kill of GO increased more gradually and plateaued beyond 12 h in the stage of 70 s % kill.

The time dependence of killing curve of *E. coli* was also investigated (FIG. 9). The % kill by QC and GO-QC reached nearly 100% after 4 h, while the % kill of GO increased more gradually and plateaued beyond 12 h at around 70+% kill.

Figure 8A:
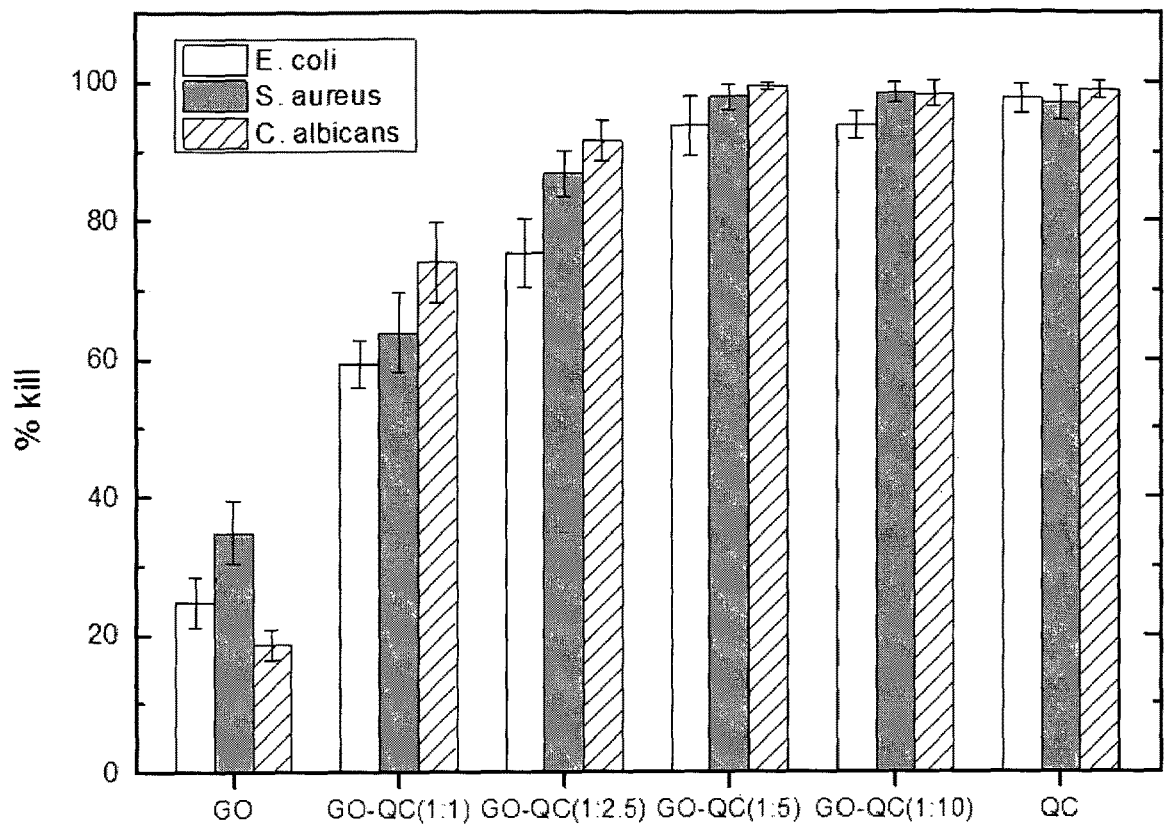
FIG. 8A is a graph showing killing rate of microbes of E. coli, S. aureus, and C. albicans after incubation with GO, QC and GO-QC series (100 μg $ml^{-1}$) for 1 h at $10^8$ CFU $ml^{-1}$. Y-axis: % kill; x-axis: GO; GO-QC (1:1); GO:QC (1:2.5); GO:QC (1:5); GO:QC (1:10); and QC.
Figure 8B:
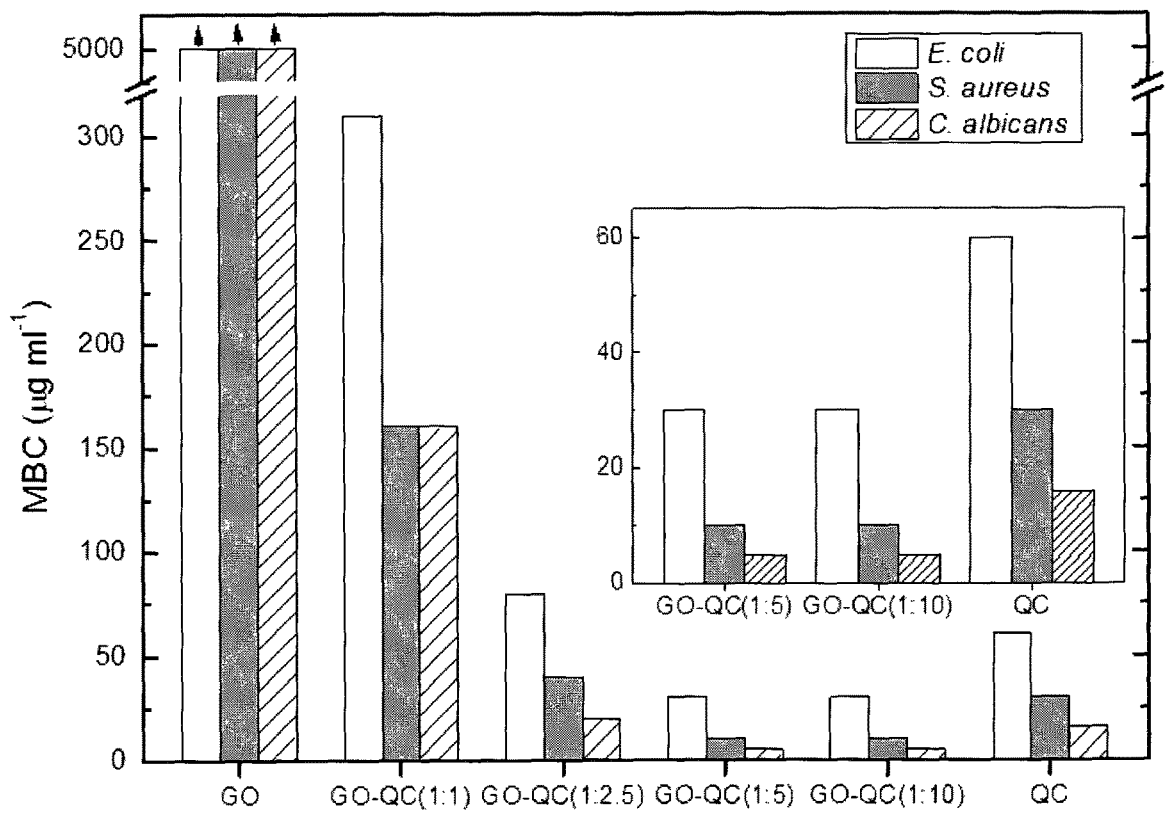
FIG. 8B is a graph showing minimum bactericidal concentrations (MBC) expressed in μg $ml^{-1}$ of E. coli, S. aureus, and C. albicans for GO; GO-QC (1:1); GO:QC (1:2.5); GO:QC (1:5); GO:QC (1:10); and QC. Insert is an expanded view of the graph for GO-QC (1:5); GO-QC (1:10); and QC.
Figure 8C:
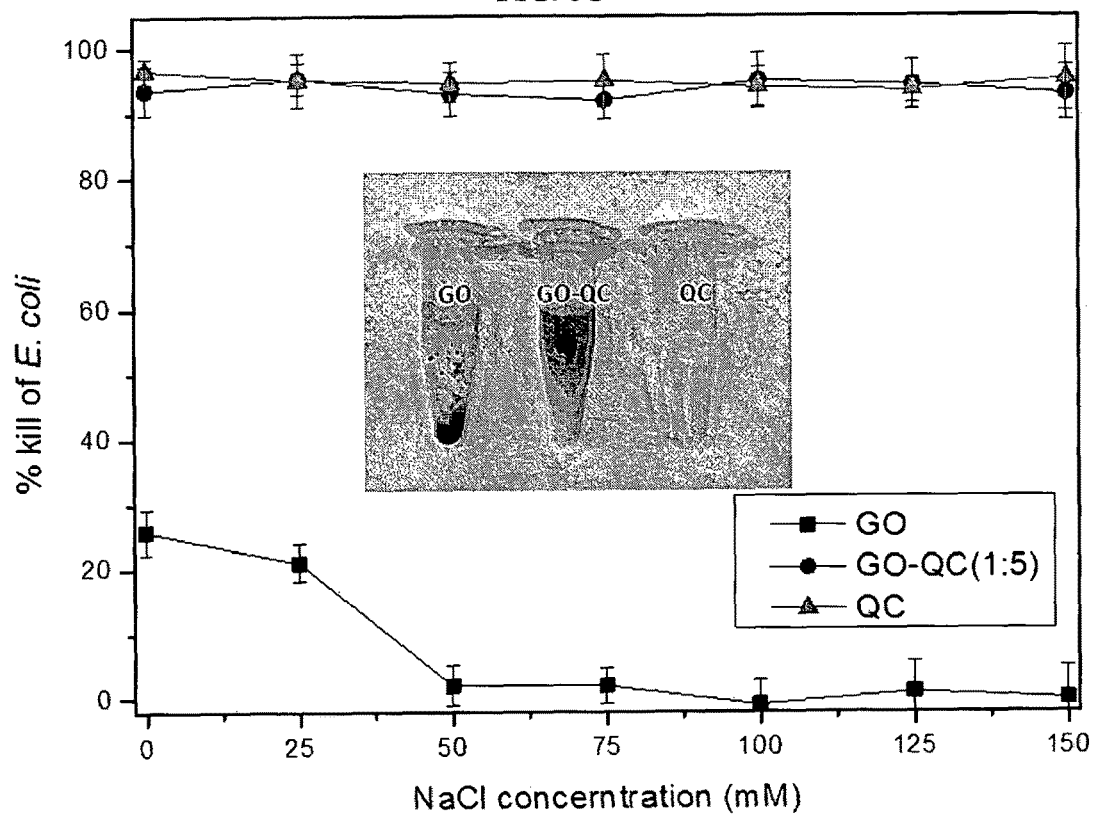
FIG. 8C is a graph showing antimicrobial activity of GO, QC and GO-QC (1:5) (100 μg $ml^{-1}$) in the presence of NaCl for 1 h, and the photographs of GO, QC and GO-QC (1:5) (100 μg $ml^{-1}$) dispersions/solution in presence of NaCl (150 mM) for 1 h. Y-axis: % kill of E. Coli; x-axis: NaCl concentration (mM).

The minimum bactericidal concentrations (MBC) of GO, QC and GO-QC were also determined (FIG. 8B and Table 1). The QC solution shows good antibacterial activity with MBCs of 60 µg ml$^{-1}$ and 30 µg m$^{-1}$ for *E. coli* and *S. aureus* respectively; it shows even better antifungal activity with a MBC of 16 µg m$^{-1}$ for *C. albicans*. The pristine GO does not show bactericidal activity at the concentration range up to 5000 µg ml$^{-1}$. With the GO-QC (1:5) nanohybrid, the MBC values are in the range of 5-30 µg ml$^{-1}$, which are lower than those of QC molecules.

The MBC results of the GO-QC nanohybrids are surprising superior to those of the polymer QC alone and this is contrary to what is usually observed with immobilization. This is probably due to the large density of immobilization, chemical compatibility of the QC polymer with the cell wall and also the "kite" nature of the immobilized polymer. As with the % kill, the MBCs plateaued with GO-QC (1:5) and (1:10). The combination of QC with GO in a nanohybrid enhances the biocidal potency.

Example 8

Antimicrobial Activity in the Presence of Salts

Ability to retain antimicrobial activity in the presence of salts is important to broaden the use of GO nanosheets for various antimicrobial applications, for example, in ionic physiological environments. Antimicrobial peptides, for example, are strongly disadvantaged by their salt-intolerant behavior, which impedes their development as coating agents. Although the hydrophilic oxygenated groups on the GO nanosheets can help with dispersion stability in water, the Van der Waals interactions that exist among the sheets can still readily induce aggregation of them. In the presence of counter ions such as $Na^+$, which are capable of binding to the anionic oxygenated groups and neutralize it, thus resulting in aggregation.

Figure 10A:
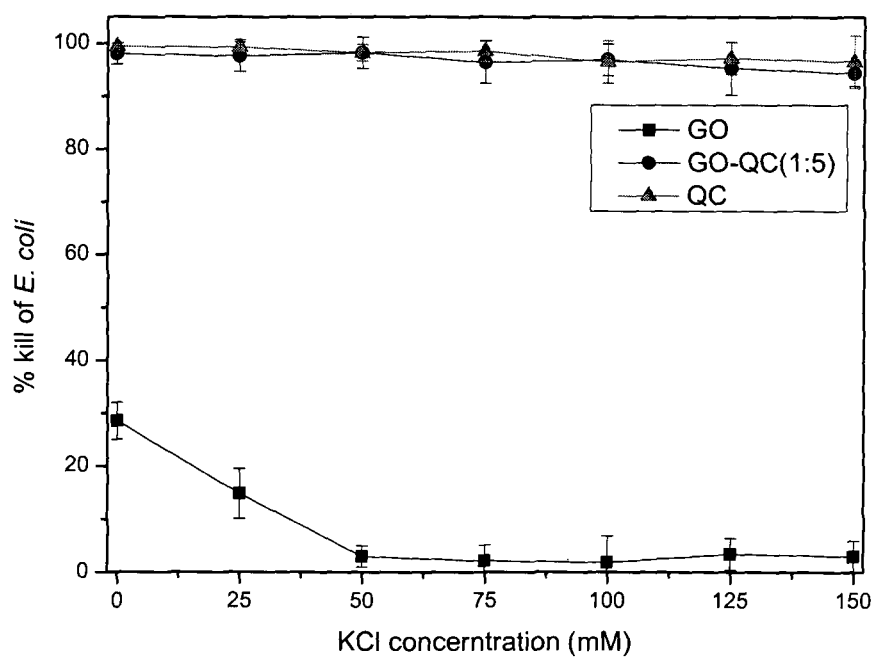
FIG. 10A is a graph showing antimicrobial activity of GO, QC and GO-QC (1:5) (100 μg $ml^{-1}$) in the presence of potassium chloride (KCl) for 1 h.
Figure 10B:
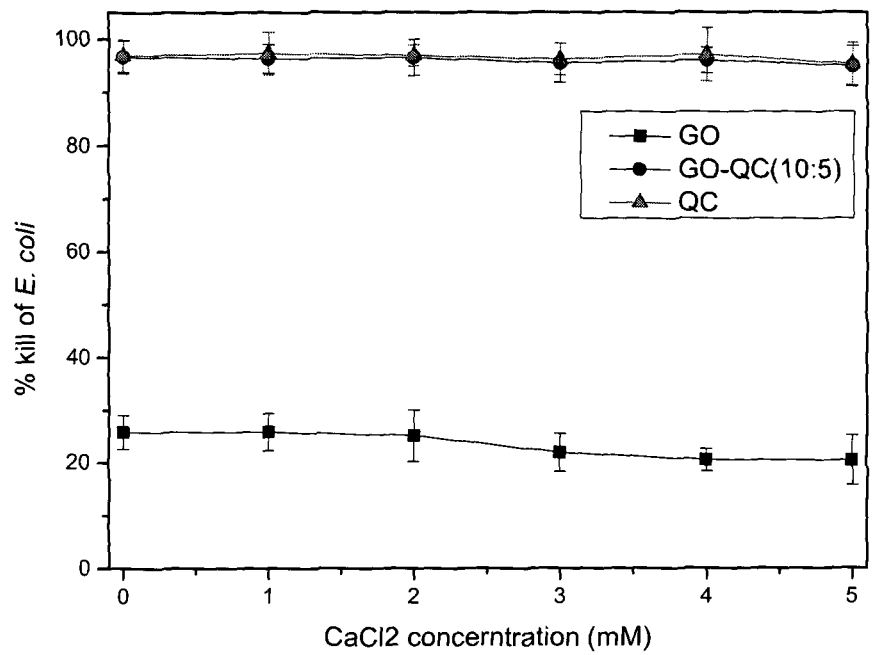
FIG. 10B is a graph showing antimicrobial activity of GO, QC and GO-QC (1:5) (100 μg $ml^{-1}$) in the presence of calcium chloride ($CaCl_2$) for 1 h.
Figure 10C:
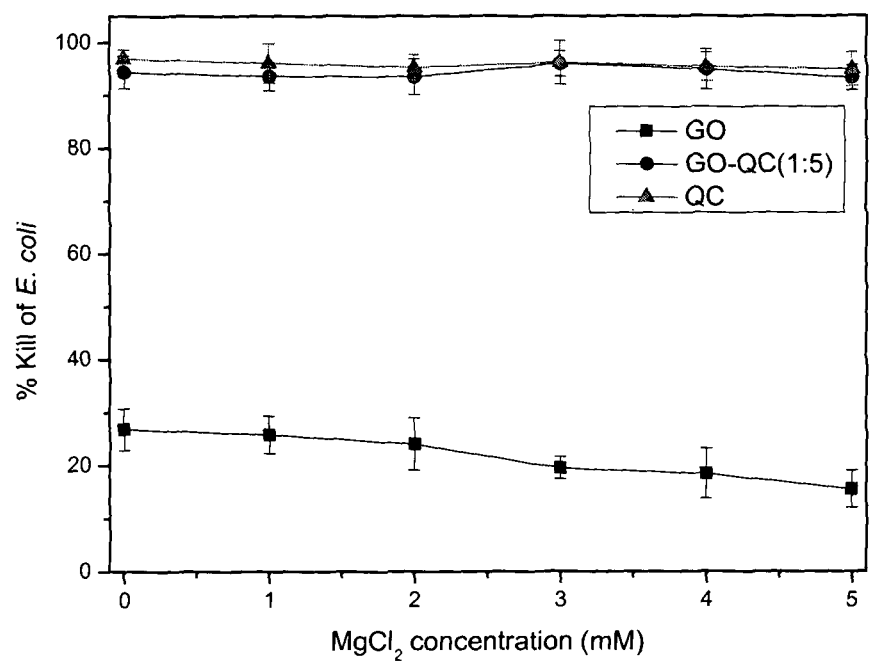
FIG. 10C is a graph showing antimicrobial activity of GO, QC and GO-QC (1:5) (100 μg $ml^{-1}$) in the presence of magnesium chloride ($MgCl_2$) for 1 h.

GO-QC(1:5) and QC also retain their antimicrobial activities, contrary to GO, in the presence of physiologically important salts, including NaCl (FIG. 8C) and KCl, $CaCl_2$ and $MgCl_2$ (FIG. 10A to FIG. 10C).

Similar with NaCl, GO lose its antimicrobial activity along the addition of KCl from 0 mM to 150 mM as shown in FIG. 10A. The antimicrobial activity of GO-QC and QC is retained at the KCl concentration up to 150 mM. Biological concentrations of divalent ions such as $Mg^{2+}/Ca^{2+}$ are much lower than those of monovalent ions; the testing range for these two divalent ions were 0 to 5 mM.[1] The antimicrobial activity was not affected by adding $Mg^{2+}/Ca^{2+}$ up to 5 mM, while the % kill of GO for *E. coli* decrease slightly along with the increasing divalent ions, as shown in FIG. 10B and FIG. 10C.

The GO-QC hybrid is salt-insensitive, just like pristine QC, because the microbial killing action does not depend on secondary conformations but the cationic charge.

Example 9

Mechanism of Action Studies

The mechanism of killing of the QC-coated graphene-supported nanohybrid is thought to be by membrane disruption and also physical damage. The morphological changes of *E. coli* cells before and after contact with QC, GO and GO-QC (1:5) solution/dispersion (100 μg $ml^{-1}$) were investigated by field emission scanning electron microscopy (FESEM) (FIG. 11 and FIG. 12).

Figure 11A:
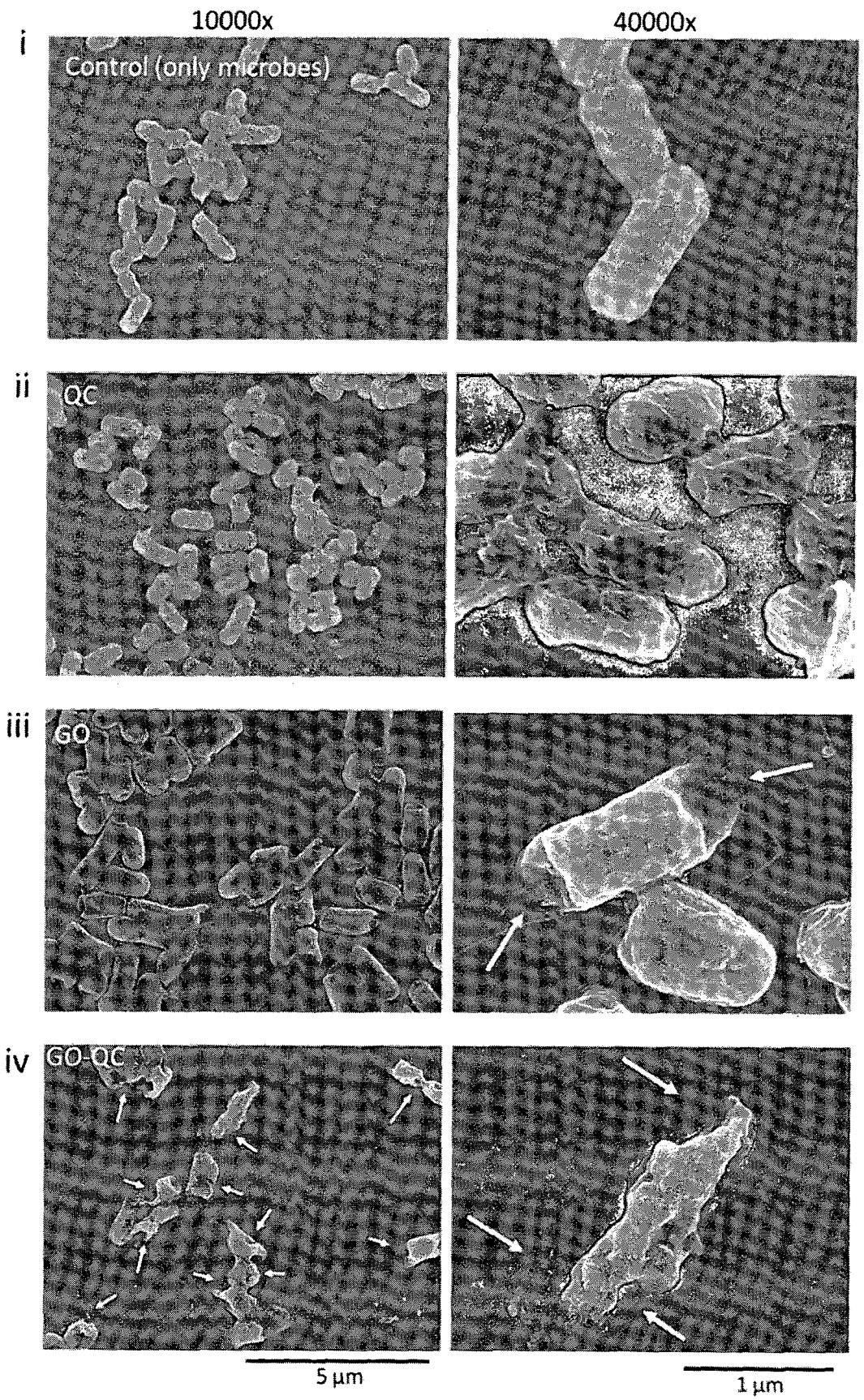
FIG. 11A shows FESEM images depicting morphology of E. coli (i) untreated control, treated with (ii) QC, (iii) GO and (iv) GO-QC (1:5) at 100 μg $ml^{-1}$ for 1 h, with magnification of 10000× and 40000× (scale bar denotes length of 5 μm and 1 μm respectively).
Figure 11B:
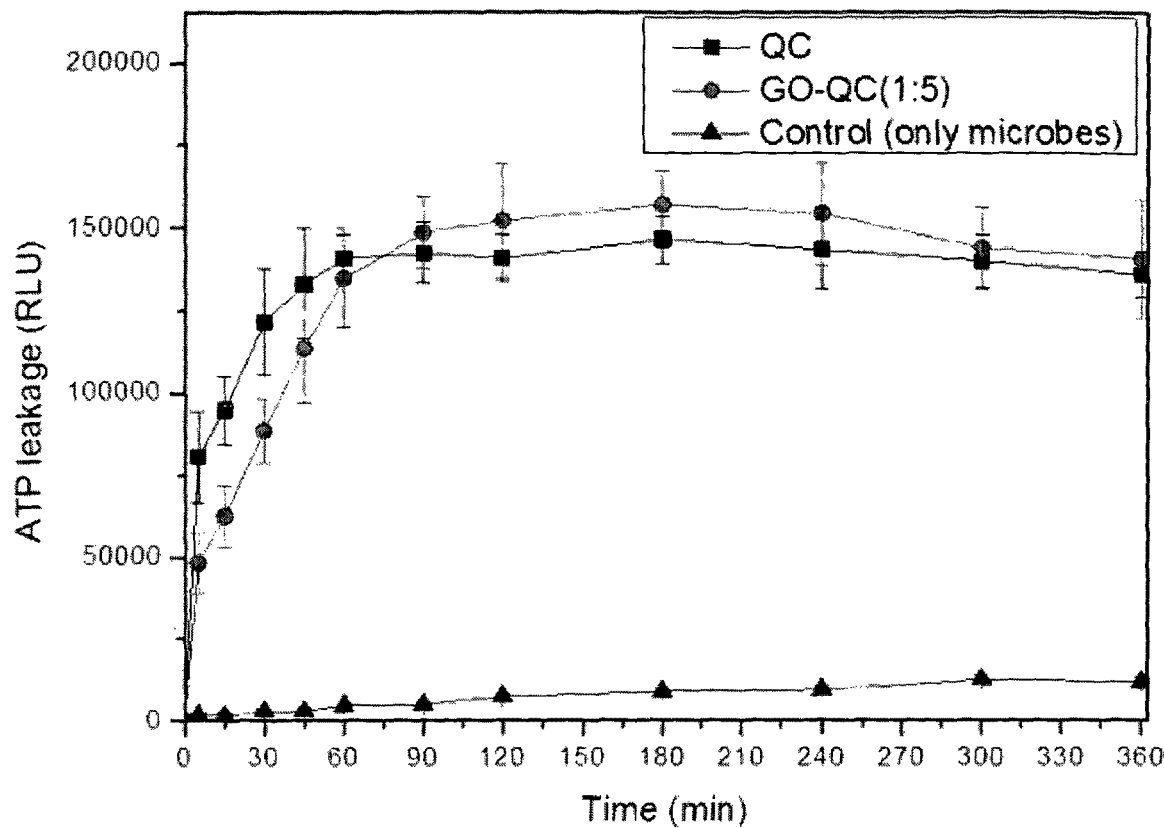
FIG. 11B is a graph depicting adenosine triphosphate (ATP) leakage induced by QC and GO-QC (1:5) as a function of time.
Figure 11C:
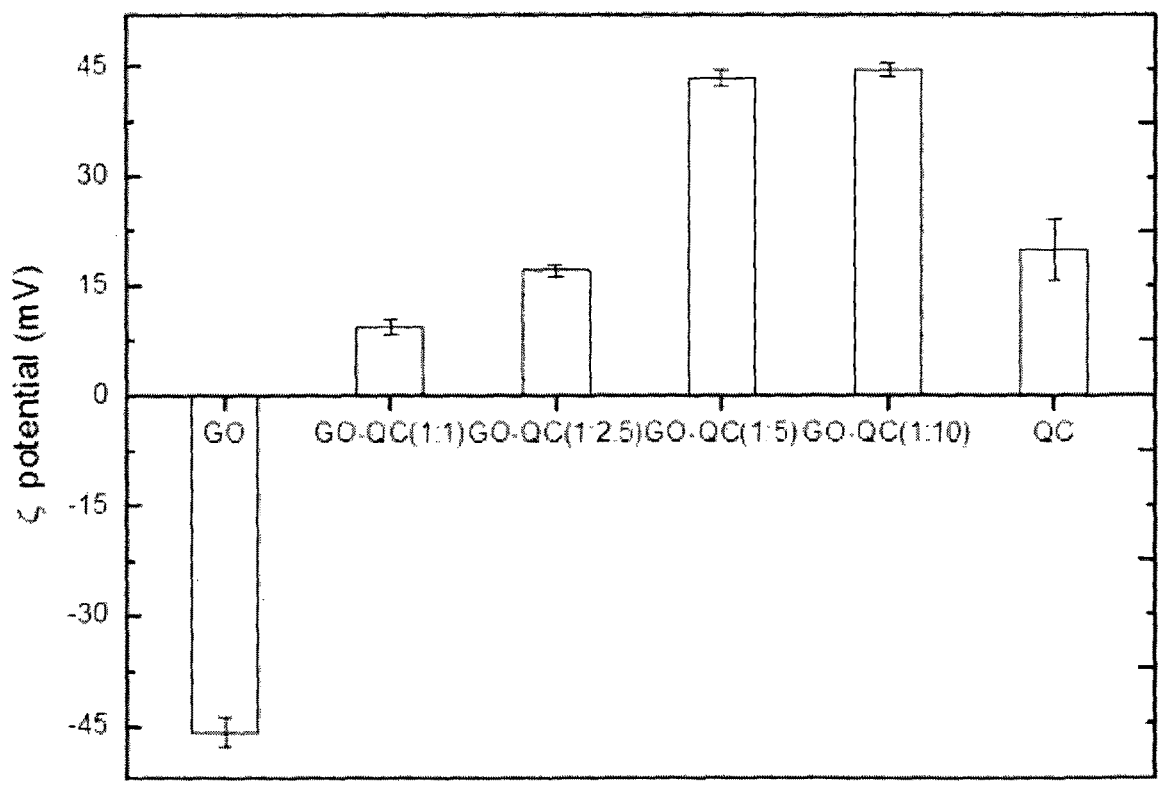
FIG. 11C is a graph showing zeta potential (mV) of GO, QC and GO-QC series of GO-QC (1:1); GO:QC (1:2.5); GO:QC (1:5); GO:QC (1:10).
Figure 12A:
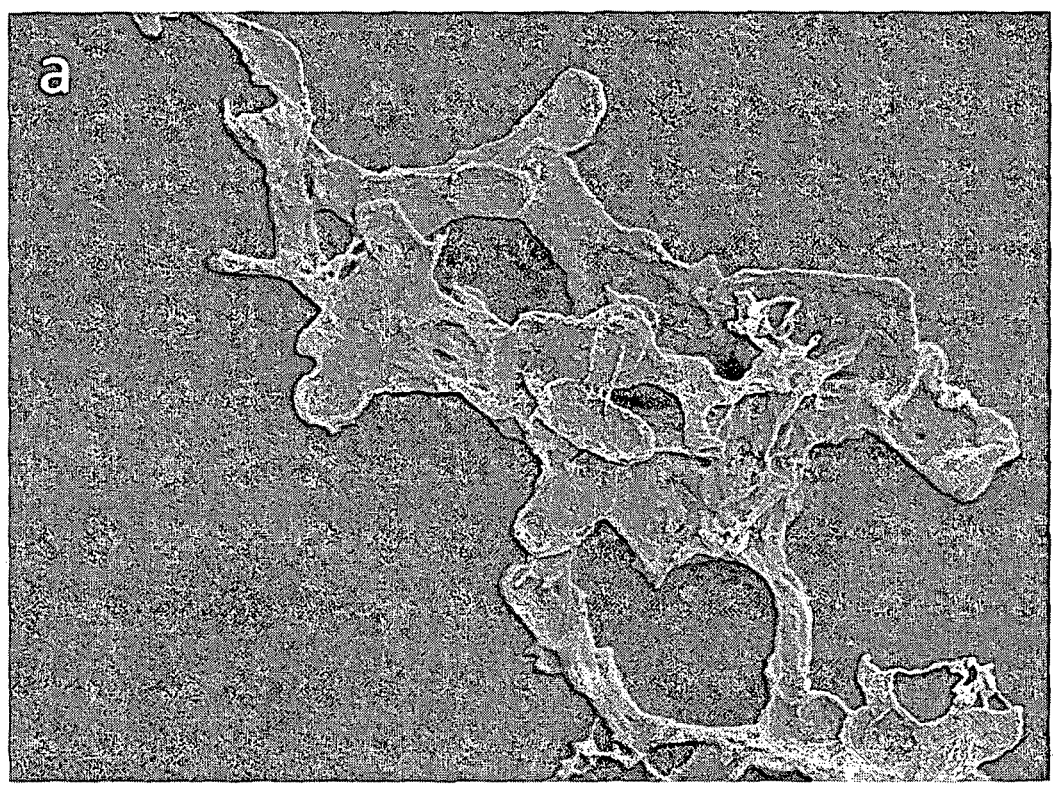
FIG. 12A is FESEM observation of E. coli cells after contact with GO-QC (1:5) at 0 min.
Figure 12B:
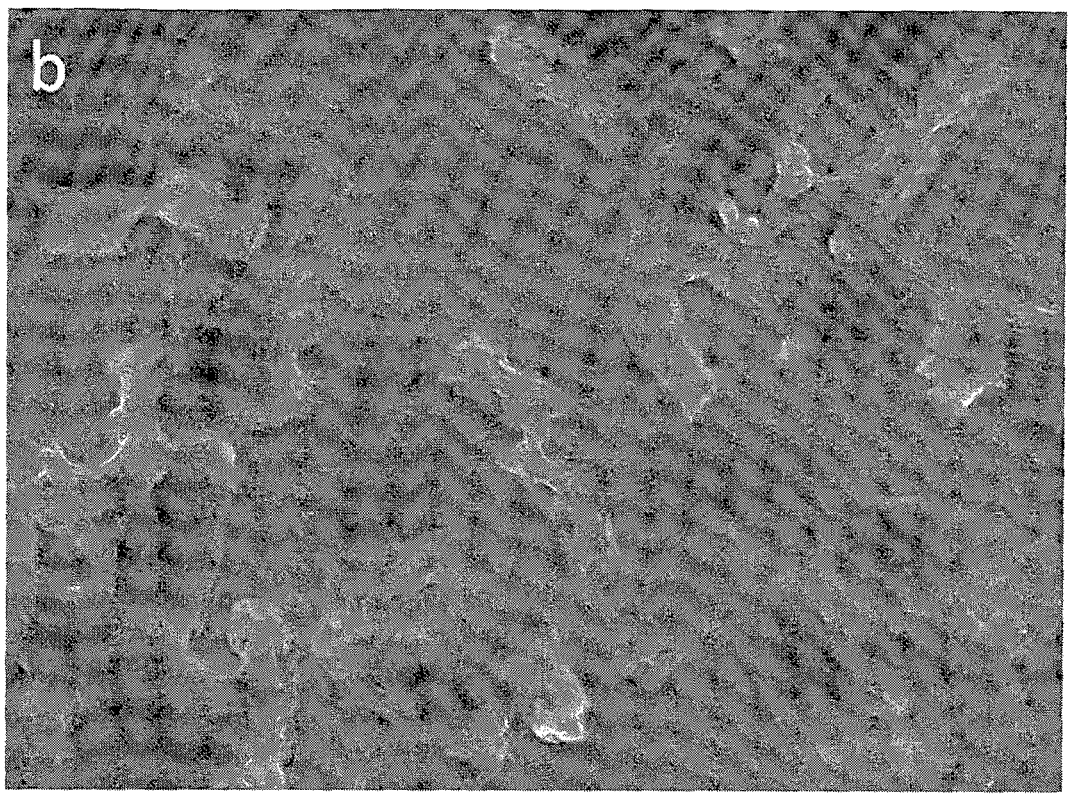
FIG. 12B is FESEM observation of E. coli cells after 1 h contact with GO-QC (1:5). As shown in the figure, the morphology of E. coli cells was changed.
Figure 12C:
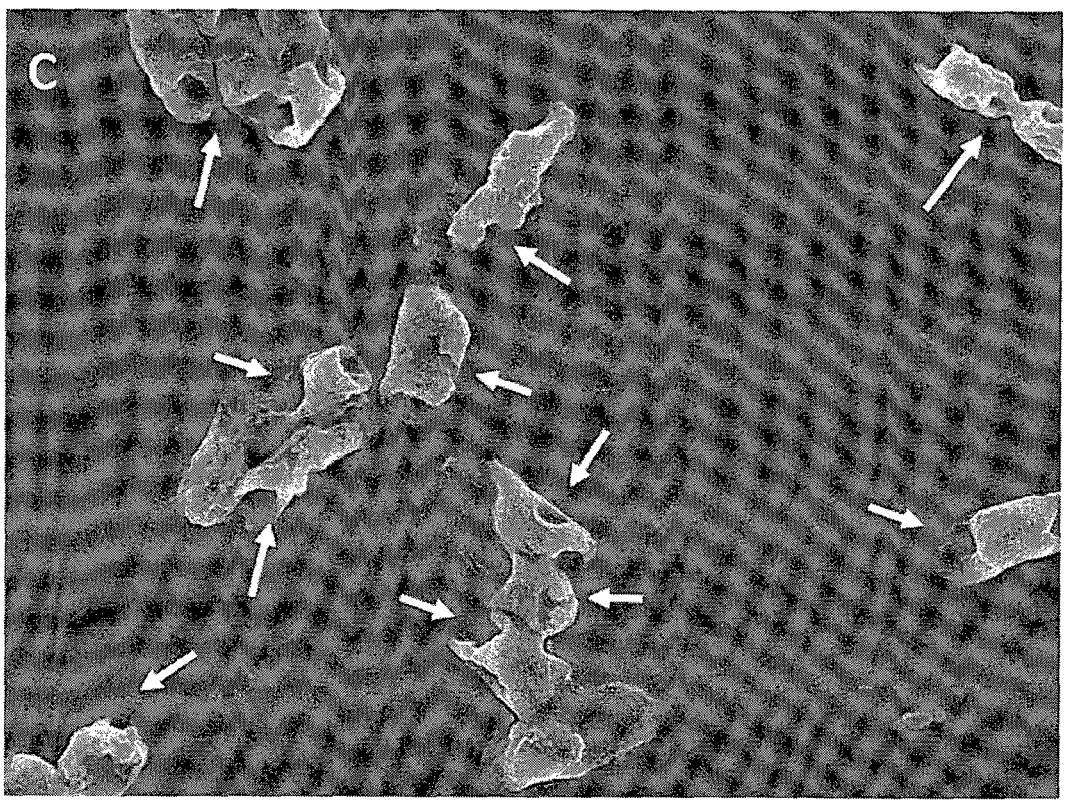
FIG. 12C is FESEM observation of E. coli cells after GO-QC nanohybrids were removed by centrifugation. Damages on bacteria membrane are indicated by the arrows.

QC-treated *E. coli* cells (FIG. 11A (ii)) shows wrinkled cell surfaces compared to the smooth surfaces of untreated control cells (FIG. 11A (i)). GO-treated *E. coli* cells, on the other hand, are found to have physical defects at the two ends of the cell (arrows in FIG. 11A (iii)), which is likely to be produced by the sharp nanoflakes. GO-QC (1:5)-treated cells shows even more drastic morphological changes compared to QC and GO individually: distinct damages (or holes) on the cells can be clearly seen (arrows in FIG. 11A (iv)), and the cell envelopes appear severely collapsed, suggesting loss of cell contents into the environment. Disruption of the cell membrane can be verified by detecting the released ATP into the extracellular environment which would be stained with BacTiter-Glo luminescence kit. As shown in FIG. 11B, there is significantly luminescence increasing after contact with QC and GO-QC, corroborating with the FESEM observation of morphological changes that suggest that membrane disruption occurs. Thus both the FESEM study and ATP leakage assay supported that GO-QC nanohybrid are able to disrupt the microbial membrane.

Without wishing to be bound by theory, it is postulated that the improved MBC (and selectivity) of GO-QC nanohybrid is due to the higher areal charge density that QC immobilized on GO presents to the cell wall, compared with what exposure to solution QC can produce. Zeta potential measurements show that GO is negatively charged (−45.78±1.93 mV) but the GO-QC are cationic. The zeta potential of GO-QC increased from 9.31±11.04 mV to 44.49±0.97 mV with increasing GO:QC ratio from 1:1 to 1:10 respectively, corroborating that the GO nanoflakes are successfully grafted with cationic polymer.

More interestingly, the zeta potentials of GO-QC (1:5) and (1:10) (43.37±1.18 mV and 44.49±0.97 mV respectively) are even higher than that of QC (20.01±4.20 mV), confirming the higher areal charge density hypothesis. The QC molecule is present at high areal concentration on the GO-QC surface compared to being evenly distributed in QC solution. It is postulated that the high QC areal concentration on the GO-QC nanohybrid makes electrostatic induced disruption of the microbe cell wall more effective, hereby decreasing the MBC values to even below those of pure QC.

Figure 11D:
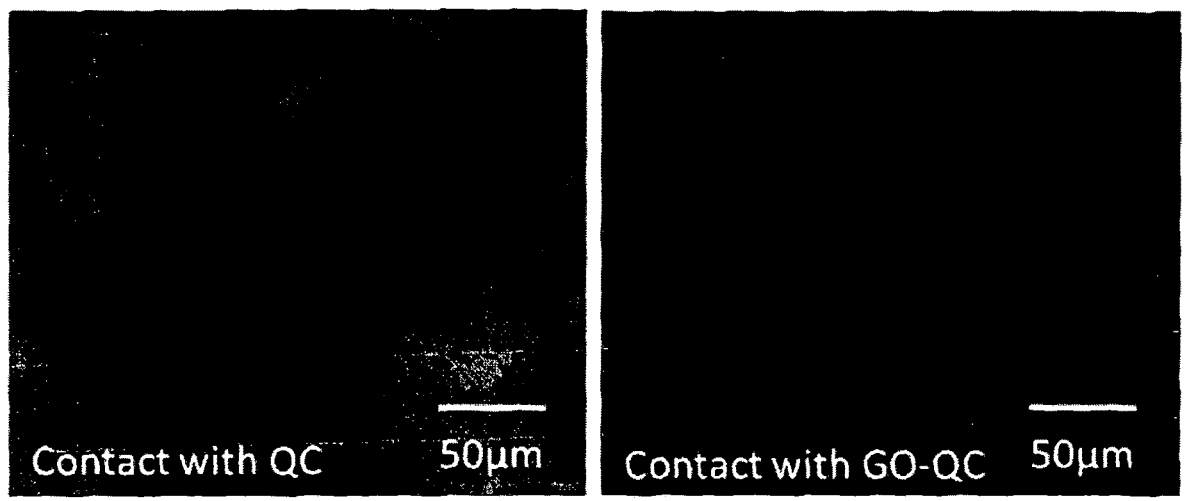
FIG. 11D depicts a fluorescence study. The bacteria pellet separated by centrifugation were stained after contact with QC solution, but not stained after contact with GO-QC. Both GO-QC and QC molecules were conjugated with a fluorescence dye (Texas Red-X).

Although the killing is electrostatic driven in both QC and GO-QC, there are significant differences in the penetration depth of both materials and the interaction between GO-QC/QC and bacteria cells was investigated by a fluorescence study. Both GO-QC and QC were conjugated with a fluorescence dye (Texas Red-X) firstly, and then the labeled materials were incubated with bacteria. After 1 h incubation, the bacteria were separated by centrifugation (2000×g, 10 min) and observed under fluorescence microscopy. Interestingly, bacteria incubated with QC-Texas Red were stained red with the fluorescence dye, while GO-QC-Texas Red was not able to stain the cells (FIG. 11D). This result indicates that bacteria cell walls absorb the QC molecules, but were not able to absorb the 2D GO-QC nanohybrids. QC molecules are in solution form and can be absorbed into the bacterial cell wall. The 2D GO-QC nanohybrid does not physically penetrate the bacterial cell cytoplasmic membrane; instead it likely exerts an electrostatic effect leading to cytoplasmic membrane disruption at some distance from the membrane. Since the GO-QC is not internalized by bacteria, it can remain in suspension and be separated from the bacteria by centrifugation so that the suspension retains its antimicrobial efficacy after multiple uses.

Example 10

Hemolytic Activity of Human Red Blood Cells

Hemolytic activity of human red blood cells (RBCs) is an important criteria in the biocompatibility determination of antimicrobial materials. The significant hemolytic activity of GO has been reported, which limits its applications in the biomedical area.

Human erythrocytes were collected by centrifugation (at 1,000×g for 10 min) of 5 ml fresh blood from a healthy donor (male, age 25). The separated erythrocytes were then washed thrice with Tris buffer before diluting to a final concentration of 5% (v/v). GO and GO-QC solutions (50 μl)

at a range of concentration series were mixed with the erythrocytes stock (50 µl) and added to a 96-well microplate. The samples were shaken in an incubator at 37° C. for 1 h at a shaking speed of 150 rpm. After incubation, the microplate well contents were then centrifuged (at 1,000×g) for 10 min. After centrifugation, the supernatant (80 µl) was added to the wells of a new 96-well microplate and diluted with an equal amount of the Tris buffer to get a final volume of 160 µl. The absorbance of the solution, at 540 nm, was read by a microplate spectrophotometer (BIO-RAD Benchmark Plus, US). 0.1% Triton X-100 served as the positive control while Tris buffer served as the negative control. The hemolysis percentage was obtained from the following equation:

Hemolysis (%)=[$(A_p-A_b)/(A_t-A_b)$]×100% where $A_p$ is the absorbance value for the GO or GO-QC containing sample, $A_t$ is the absorbance value for the positive control, and $A_b$ is the absorbance value for negative control.

The concentration of GO and GO-QC required to incur 50% hemolysis of RBCs ($HC_{50}$) was measured (Table 1). The $HC_{50}$ of pristine GO is 310 µg ml$^{-1}$, while the GO-QC series generally showed a much higher $HC_{50}$. GO-QC (1:1) and (1:2.5) has their $HC_{50}$ at 2,500 and 5,000 µg ml$^{-1}$ respectively, the higher QC ratio of (1:5) and (1:10) show larger $HC_{50}$>5,000 µg ml$^{-1}$. Our previous results demonstrate that quaternized chitosan are biocompatible materials having low hemolytic activity, and its grafting to GO has further reduced the hemolytic activity of the GO nanosheets. Compare with their minimum inhibitory concentration which inhibits more than 90% microbe growth ($MIC_{90}$), the selectivity of the desired GO-QC (1:5) nanoflakes is calculated to be greater than 125.

Example 11

Preparation and Antimicrobial Activity of GO-QC Coating

GO-QC nanosheets were fabricated as a transparent nanoporous antimicrobial surface coating by a sol-gel method, where GO-QC sol was spin-coated on an oxygen plasma treated glass surface, and the coating was formed by subsequent gelation (FIG. 2).

Typically, sols were prepared by adding 0.1 ml tetramethyl orthosilicate (TMOS, Sigma-Aldrich) to a 5-mL vial containing a mixture of ethanol (1 ml) and GO/GO-QC suspension in water (1 ml). The vials were capped and the resulting sols were left at room temperature for one day before being used for the coating fabrication. Glass cover slips were cleaned by bath ultrasonication first in NaOH (1M) and then in acetone each for 30 min. After drying under a nitrogen flow, the slips surface were activated with oxygen plasma (March PX-500, Germany) at a radio frequency of 13.56 MHz, gas flow rate of 100 sccm, pressure of 500 mTorr and power of 200 W for 10 minutes. A few drops of GO or GO-QC/TMOS Sols were then deposited on the plasma activated cover slips by spin-coating at 6000 rpm for 2 minutes. The coated thin sol films were gelled at 70° C. in an air oven overnight, followed by curing at 130° C. for 2 h under a controlled argon gas flow in a tube furnace (2° C./min heating and 5° C./min cooling rates).

Antimicrobial assay on this coating was performed on GO and GO-QC coating, and the plasma-treated glass slip was used as a control.

The GO/GO-QC coated glass cover slips were placed in 24-well plates and sterilized under UV light for 1 day. 10 µl bacterial inoculums were pipetted onto the coating surface, then another coated slip was covered on it make the inoculums spread and contact uniformly between the coatings. Pristine glass slips were used as a control. The inoculated slips were incubated at 37° C. (28° C. for fungi) and a relative humidity of not less than 90% for 1 h. After incubation, 1 ml of neutralizing broth was added to each well to recover the microbe survivors. A series of 10-fold diluted samples was prepared and plated out in LB agar (YM agar for fungi). The plates were incubated at 37° C. (28° C. for fungi) overnight and the colony forming units counted. The log reduction of cells was calculated as below equation:

Log reduction=Log(cell count of control)−Log(survivor count on sample)

Figure 2E:
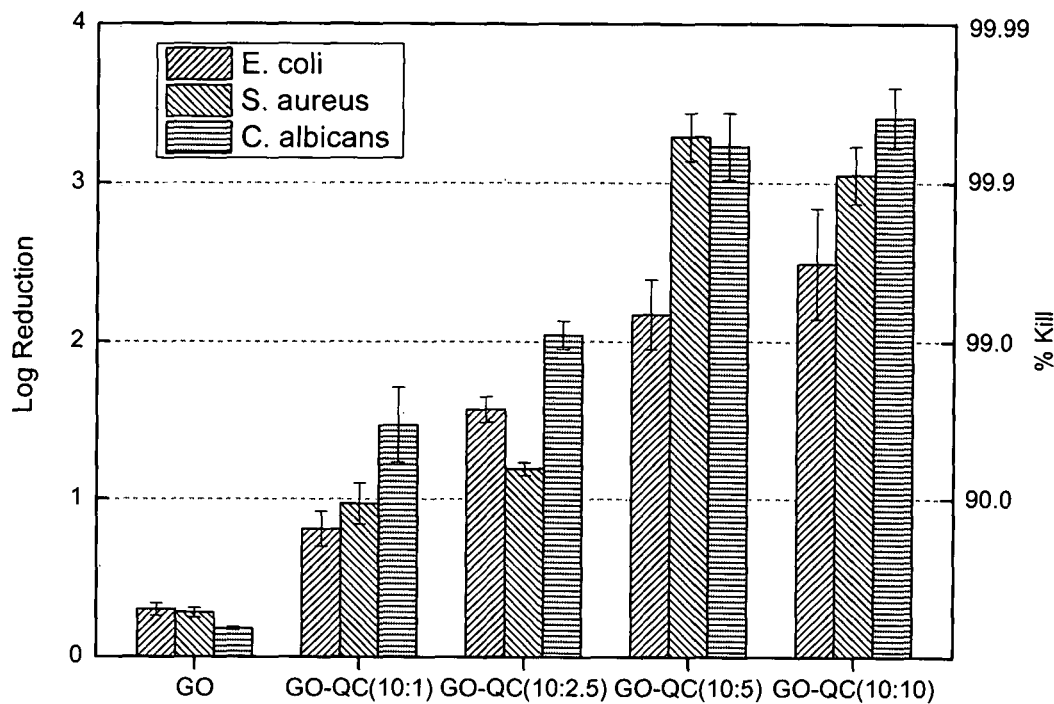
FIG. 2E is a graph showing Log reduction and % Kill of E. coli, S. aureus, and C. albicans after contacting with GO and GO-QC coatings of GO; GO-QC (10:1); GO:QC (10:2.5); GO:QC (10:5); and GO:QC (10:10).
Figure 3:
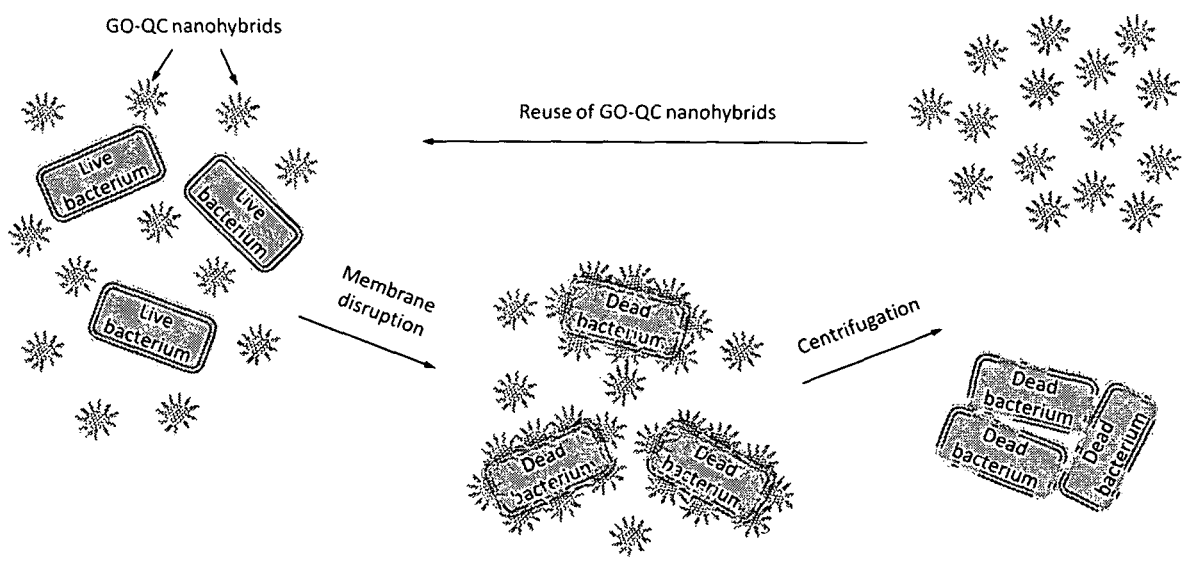
FIG. 3 is a schematic diagram depicting cationic GO-QC nanohybrid's disruption on the anionic microbial envelope leading to cell death.

The log reduction of three microbes was recorded by colony plate counting. GO only shows a log reduction of 0.18±0.01 to 0.30±0.04, while GO-QC shows a much higher reduction; the log reductions of GO-QC (1:5) and GO-QC (1:10) above 2 indicates inhibitory values which are larger than 99% (FIG. 2E).

The carboxyl groups on GO nanosheets render it anionic, which is same charge state as microbial membranes. The occurrence of electrostatic repulsive forces between GO and microbial cells can therefore impede the rate at which they make contact, which explains the more gradual manner GO damages membranes. Quaternized chitosan; which are cationic polysaccharides, changes the charge state of GO from anionic to cationic, when functionalized to the GO nanosheets. In cationic GO-QC dispersions, the cationic nanosheets are electrostatically drawn to the anionic microbial cells, where both the cationic charge and sharp edges of the GO-QC nanosheets synergistically disrupt the anionic microbial membranes rapidly and efficiently. GO-QC therefore shows enhanced antimicrobial activity than pristine GO. The increase in charge state of GO-QC did not compromise biocompatibility properties of the nanosheets, as indicated by an improved $HC_{50}$ for the GO-QC series compared to GO alone. The coating of GO-QC is efficiently antimicrobial and transparent, which opens the way for the use of GO-QC nanosheets for antimicrobial applications in biomedical and other fields.

The graphene oxide-graft-quarternized chitosan (GO-QC) nanosheets thus prepared have several advantages over pristine GO. Firstly, modification of GO with QC polymers improves dispersion of the material in the aqueous environment thus overcoming aggregation tendencies of GO in solution. Further, use of cationic quarternized chitosan is aimed to increase the charge of GO, for further enhancement of its antimicrobial activity. As chitosan and its derivatives are biocompatible materials, use of chitosan to modify graphene oxide may circumvent toxicity induced by the GO nanosheets.

In the experiments carried out, the antimicrobial activity of pristine GO, QC, and GO-QC was investigated for three microbes: Gram-negative bacteria *Escherichia Coli* (*E. coli*), Gram-positive bacteria *Staphylococcus aureus* (*S. aureus*), and fungus *Candida. albicans* (*C. albicans*).

Results show that the antimicrobial efficacy of GO is significantly enhanced after conjugation with QC covalently. A transparent coating of GO-QC nanosheets was fabricated by a sol-gel method on glass surface, which inhibit both Gram-negative/positive bacteria and fungi effectively.

Example 12

In Vitro Biocompatibility Study

The GO-QC (1:5) coated glass cover slips were sterilized in 70% ethanol for 1 hour before use. Human aorta smooth muscle cells (HASMC CC-2571, Lonza) were seeded to the 24-well culture plates at the density of $0.5 \times 10^5$ cells $cm^{-2}$. The culture medium was supplemented with 100 µg $ml^{-1}$ GO-QC (1:5). GO-QC (1:5) coated slips were placed into the wells with GO-QC coated side face to cell cultures when cells had adhered to the plate (about 4-5 h). The culture medium was changed every 2 days. On specified days, cells were analyzed with CCK-8 kit (Sigma, US) by the absorbance at 450 nm to determine the cell viability. Cells in TCPS wells without GO-QC coated slips were used as control. The viability of SMC was also examined with the LIVE/DEAD assay.

After specified cell culture time periods, the GO-QC coated glass slips were removed and the cells were stained with LIVE/DEAD kit (Invitrogen, US). After 45 min incubation the LIVE/DEAD dye was removed by PBS rinsing, the morphology of the cells was observed in fluorescence with an inverted optical microscope (Zeiss, Germany).

Example 13

Reusability of QC-GO Hybrid

Reuseability of QC-GO hybrid was also tested and it was found to be significantly far superior compared to either QC or GO alone.

Figure 8D:
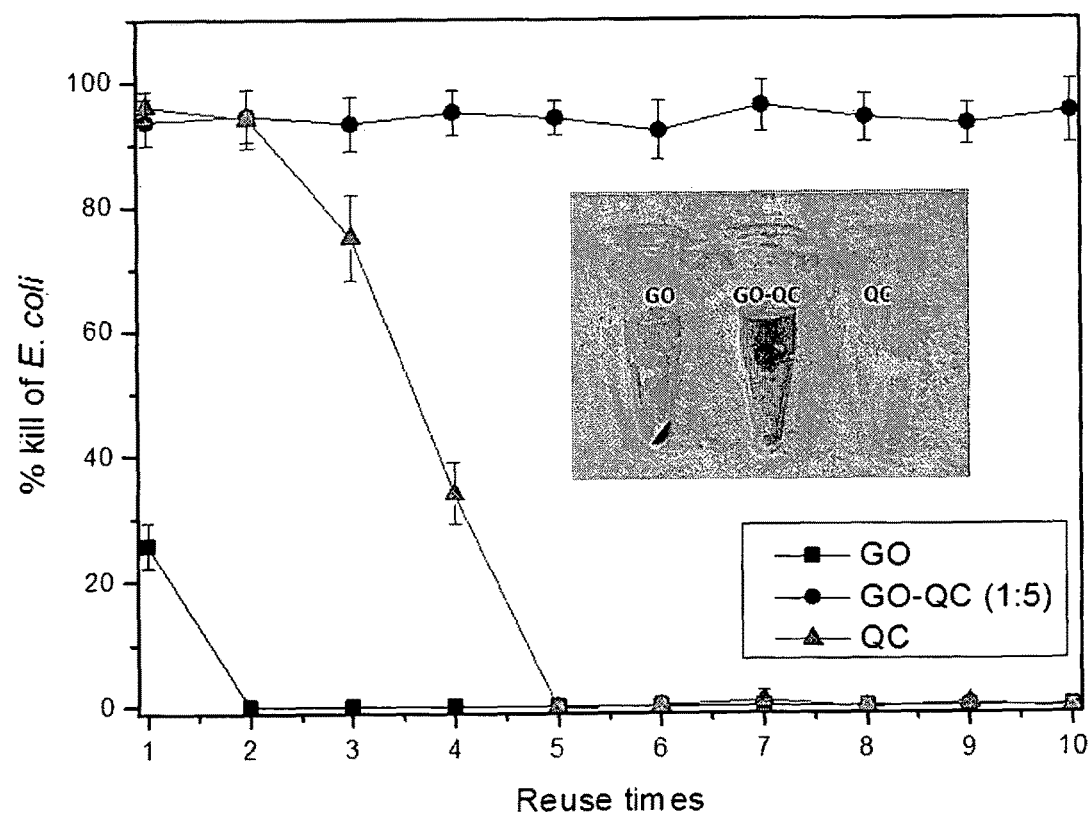
FIG. 8D is a graph showing the reusable antimicrobial activity of GO-QC (1:5) (100 μg $ml^{-1}$) for 10 times repeating challenged of E. coli, the treated bacteria was separated by centrifugation (2000×g, 10 min). Y-axis: % kill of E. Coli; x-axis: no. of times reused.

The candidate material was repeated challenged with *E. coli* at a concentration of $10^8$ CFU $ml^{-1}$. After incubation of the pathogens with the material, they were separated by centrifugation so that the bacterial cells settled down in the suspension. The pristine GO precipitated together with *E. coli* cells under centrifugation, thus losing its reusability at the $2^{nd}$ time (FIG. 8D). QC solution at the same concentration (100 µg $ml^{-1}$) only retain more than 90% kill efficacy in the first two times usage and its antimicrobial efficacy drop to near 0% with five times contact with bacteria. In contrast, the GO-QC (1:5) can be repeatedly used for at least 10 times. After *E. coli* challenge and centrifugation, the GO-QC (1:5) nanohybrid remained well-dispersed in water (FIG. 8D) and can be recovered. GO-QC (1:5) killed more than 90% *E. coli* for each round testing, and retained its efficacy in the repeat usage up to 10 times. GO-QC (1:5) killed more than 90% *E. coli* for each round of testing, and exhibited no significant decline in its efficacy during 10 uses. The reusability of the nanosuspension appears to be a unique superior property of the hybrid.

The GO-QC series generally have 50% hemolysis concentrations ($HC_{50}$) (Table 1) which are intermediate between the two controls (QC and GO).

Figure 8E:
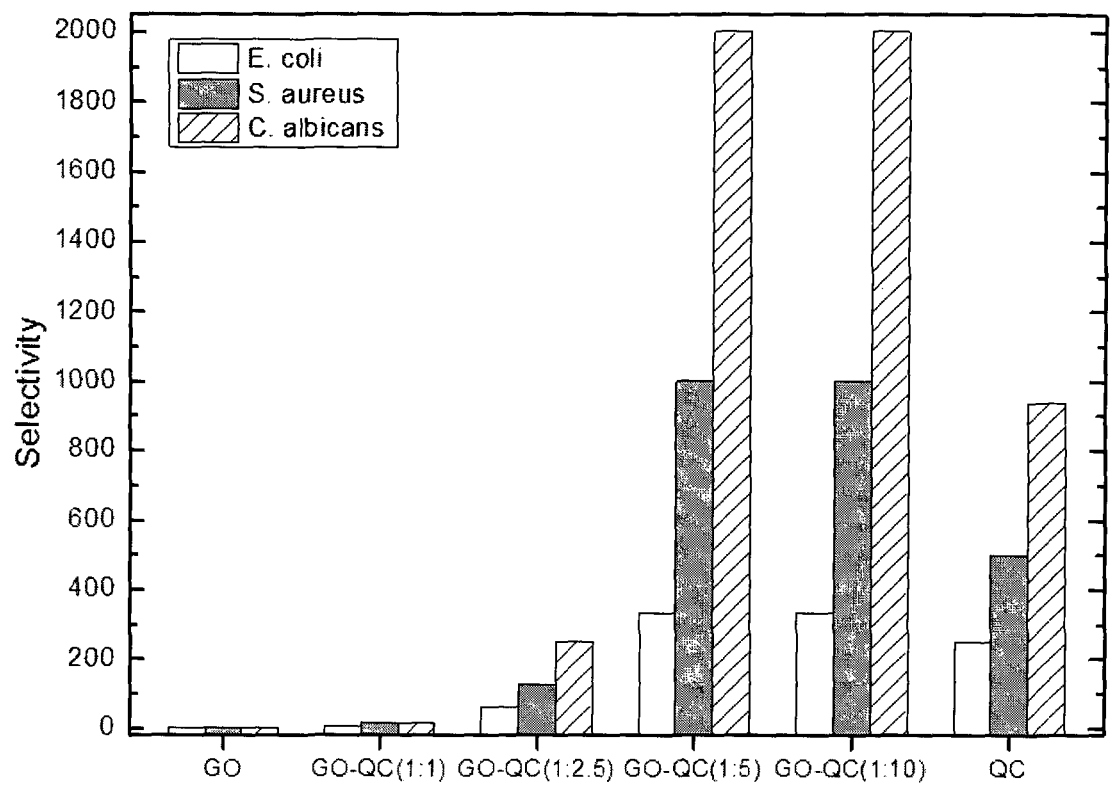
FIG. 8E is a graph showing selectivity of E. coli, S. aureus, and C. albicans for GO; GO-QC (1:1); GO:QC (1:2.5); GO:QC (1:5); GO:QC (1:10); and QC.

For example, GO-QC (1:5) and (1:10) show high $HC_{50}$ values of 10,000 µg $ml^{-1}$ while the $HC_{50}$ values of pristine QC and pristine GO were 15,000 µg $ml^{-1}$ and 1250 µg $ml^{-1}$ respectively. The selectivity (defined as $HC_{50}$/MBC) of QC-QC (1:5) is about double that of QC for the various pathogens (FIG. 8E). The significant hemolytic activity of GO is due to the sharp edges of pristine GO which are expected to be harmful to mammalian cells.

Figure 8F:
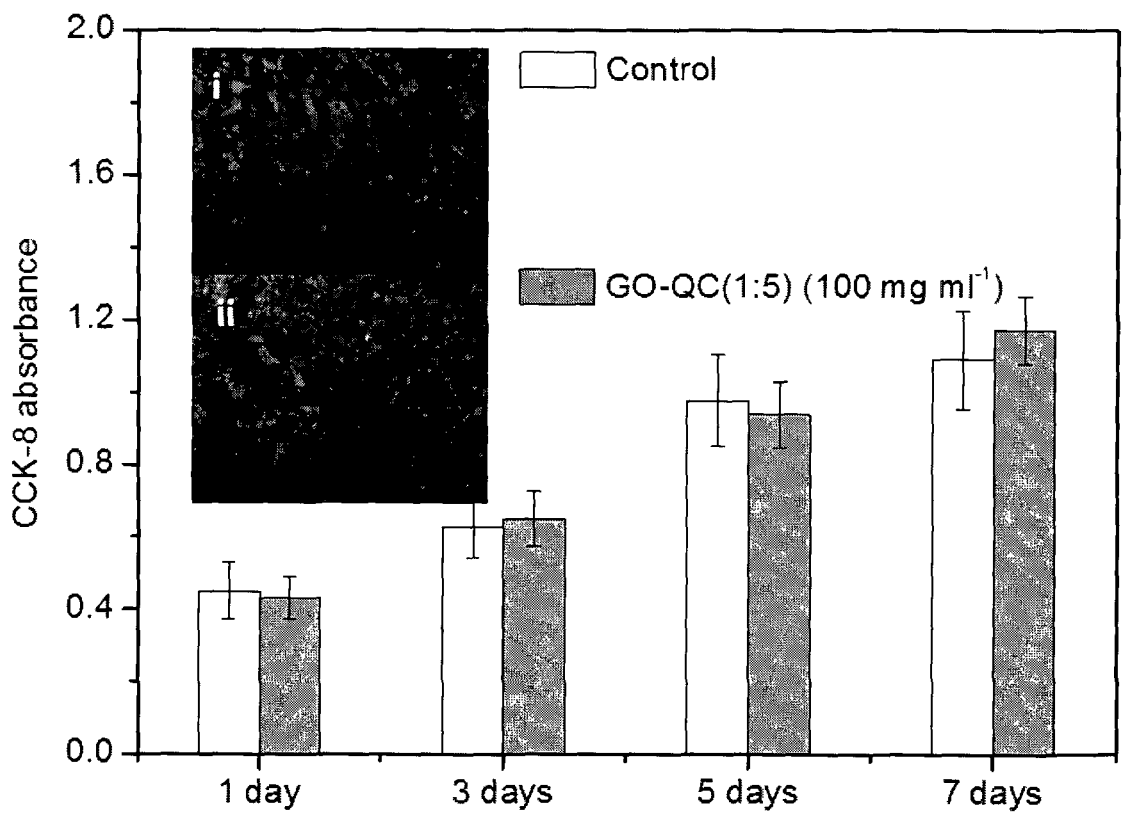
FIG. 8F is a graph showing in vitro cytotoxicity study of smooth muscle cells cultured with 100 μg $ml^{-1}$ GO-QC (1:5), the cell viability was determined by Cell Counting Kit-8 (CCK-8) assay, tissue culture polystyrene (TCPS) was used as control. (p>0.05, no significant difference). Y-axis: CCK-8 absorbance; x-axis: no. of days. Insert shows LIVE/DEAD analysis of smooth muscle cells cultured (i) without and (ii) with 100 μg $ml^{-1}$ GO-QC (1:5) for 7 days.

Chitosan derivatives, such as QC in this report, have low hemolytic activity and low toxicity to mammalian cells. The presence of QC molecules surrounding the GO-QC nanohybrid likely function as a biocompatible protection layer which lowers the physical damage to mammalian cells so that GO-QC shows a much improved $HC_{50}$ compared with pristine GO. It has been shown that human aorta smooth muscle cells (SMCs) exposed to the GO-QC (1:5) (100 µg $ml^{-1}$) were viable and statistically insignificant from the exposure to the tissue culture polystyrene (TCPS) dish control (FIG. 8F, p>0.05, no significant difference).

Example 14

Discussion

Grafting of the GO nanomaterial by cationic QC serves various functions. Firstly, modification of GO with water soluble cationic QC improves the dispersion of the resulting nanohybrid in aqueous environment, thus overcoming the aggregation tendencies of GO in solution. Secondly, the cytotoxicity of GO nanoflakes was obscured by the grafting with the biocompatible chitosan derivative at its sharp edge. GO nanoflakes disrupt microbes' cell membrane by their sharp edges, leading to the loss of membrane integrity and leakage of inner components, and eventually cell death. Thirdly, functionalization of GO with cationic quaternized chitosan turns the charge state of GO from anionic to cationic and endows the GO-QC nanohybrid with positive charge, so that electrostatic attraction between the cationic GO-QC and the anionic bacterial cell cytoplasmic membrane would disrupt the bacteria membrane. Fourthly, chemical similarity of QC to the polysaccharide content of cell wall peptidoglycan promotes GO-QC penetration into the cell wall to bring the cationic charges near the microbe cytoplasmic membrane.

The immobilization of cationic QC molecules on GO nanoflakes with high specific area results in more concentrated positive charge than in dissolved QC, so that the high areal charge density on GO plays an important role in the enhanced antimicrobial properties. The concentration of cationic QC molecules in a small area leads to increased zeta potential and charge density. When GO-QC nanohybrids contact with microbe cells, the concentrated cationic QC molecules on the nanohybrids interact with the anionic microbial membrane more strongly than QC in solution. Thus the concentration of QC molecules on small size nanoflakes leads to improved MBC of the GO-QC (1:5) and (1:10) compared with pure QC in solution. Also, the nanohybrid shows excellent selectivity of around 333-2000, coupled with no obvious in vitro cytotoxicity towards human cells.

Antimicrobial nanoparticles made from self-assembled biodegradable block copolymers have been reported although the significant non-active block of the copolymer necessary for the micelle formation makes the minimum inhibitory concentrations on the higher side (around 5-15µM). Also, for many non-biomedical applications, reuse and retrieval also need to be considered. Unlike free molecules of QC evenly distributed in solution form, the QC molecules in GO-QC nanohybrid are concentrated on the monolayer nanoflakes. The cationic QC molecules were concentrated in a small area leading to increased zeta potential and charge density. When GO-QC nanohybrids contact with microbe cells, the concentrated cationic QC molecules on the nanohybrids interact with the anionic microbial membrane more strongly than QC in solution. Thus the concentrated QC molecules on small size nanoflakes lead to improved MBC of the GO-QC (1:5) and (1:10) compared with pure QC in solution.

More interestingly, it has been demonstrated herein that cationic nanosuspension can exert biocidal effect repeatedly which is not possible with the corresponding solution forms of the cationic polymer.

When free QC molecules in solution interact with bacteria, they are absorbed and inserted into the bacterial cell wall. The solubilized QC molecules precipitate with bacteria cells under centrifugation, depleting the solution of antimicrobial agent thus causing the remaining solution to lose its antimicrobial efficacy after repeated use. Unlike free QC molecules, QC molecules in the GO-QC nanohybrid are immobilized on GO nanoflakes which prevent their absorption by the microbes.

On centrifugation, the nanohybrid will separate from the bacteria cells and remain suspended and not precipitate together with the bacterial cells, thereby retaining its antimicrobial efficacy after repeat usage. This nanomaterial (using 2D GO) exploits the nanoscale thickness, the micron-scale lateral size, the insoluble nature of GO (so that they cannot be absorbed by the cells) and also the high charge density. When the flexible GO-QC nanoflakes wrap around the bacteria cell, their high charge will induce strong attraction of the anionic cytoplasmic membrane outer leaflet at a distance from the cytoplasmic membrane. As the QC molecules are restricted on GO nanoflakes, GO-QC nanohybrids are not able to insert into the cytoplasmic membrane. The anionic bacterial cytoplasmic membrane outer leaflet may be warped by the electrostatic interaction, or indiviual anionic molecules may be pulled out of the membrane, leading to cell death. The grafting of a killing agent, in this case a cationic polymer, on a nanomaterial (specifically graphene) appears to truly exploit the nanoscale thickness and micron-scale large lateral size and insoluble nature of the 2D GO material so that the nanohybrid is a stable suspension that has high cationic charge density.

This is the first report of a cationic nanosuspension which exerts excellent broad spectrum antimicrobial effect, as well as good in vitro biocompatibility and superior selectivity, and easy retrievability and reusability. Other antimicrobial nanosuspensions have been based on leachable active materials such as Ag. The MBC and selectivity values of the GO-QC nanohybrid are higher than other reported values for cationic nanoparticles. The nanosuspension disclosed herein is broad spectrum antimicrobial, non-contaminating and biocompatible. The GO-QC nanohybrid has better MBC and selectivity values compared with the individual components (GO or QC alone) which probably results from the high areal charge density. The latter and the insoluble form of the nanohybrid result in the superior reusability of the nanohybrid, which have hitherto not been demonstrated or observed with solution forms of cationic polymers. Further, this suspension also demonstrates the electrostatic-based membrane disruption "at a distance" which need not involve insertion into the bilayer. The atomic layer GO with high functionality enables high surface grafting density and low mass contribution of the GO carrier so that the MBC of this nanohybrid is outstanding. The combination of QC and GO also obscures the cytotoxicity of GO nanoflakes and shows improved biocompatibility of GO-QC nanohybrids compared with GO alone. Further, the insoluble character of the nanohybrid results in superior reusability. This class of antimicrobial GO-QC nanosuspension has outstanding antimicrobial application prospects in biomedical, environmental, personal care and other fields.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A hybrid nanomaterial comprising graphene oxide nanomaterial covalently conjugated to cationic quaternized chitosan, wherein the cationic quaternized chitosan prior to the conjugation is represented by formula (I)

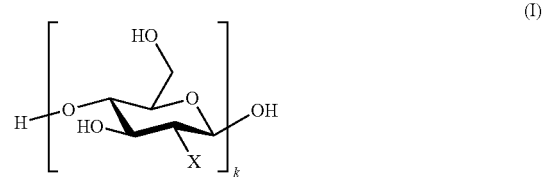

wherein
X, at each occurrence, is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$),
R$^1$ and R$^2$ are independently selected from H and C$_{1-18}$ alkyl
R$^3$, R$^4$ and R$^5$ are each independently C$_{1-18}$ alkyl, and
k is an integer from 3 to 3000;
wherein the graphene oxide nanomaterial is covalently conjugated to the cationic quaternized chitosan at an occurrence of X, wherein the occurrence of X is —NH$_2$.

2. The hybrid nanomaterial according to claim 1, wherein R$^1$ and R$^2$ are selected from H and C$_{1-18}$ alkyl; and R$^3$, R$^4$, and R$^5$ are each independently C$_{1-10}$ alkyl.

3. The hybrid nanomaterial according to claim 2, wherein R$^3$ and R$^4$ are methyl and R$^5$ is C$_{1-10}$ alkyl.

4. The hybrid nanomaterial according to claim 1, wherein the ratio of monomers with X=—N(R$^1$)(R$^2$) and X=—N$^+$(R$^3$)(R$^4$)(R$^5$) to monomers with X=—NH—C(O)—CH$_3$ is in the range of 2:1 to 5:1.

5. The hybrid nanomaterial according to claim 4, wherein the ratio of monomers with X=—N(R$^1$)(R$^2$) to monomers with X=—N$^+$(R$^3$)(R$^4$)(R$^5$) is in the range of 1:4 to 4:1.

6. The hybrid nanomaterial according to claim 1, wherein the cationic quaternized chitosan comprises dimethyldecylammonium chitosan having general formula (II)

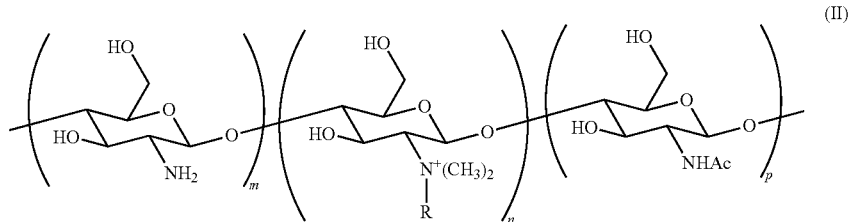

wherein

R is selected from the group consisting of —CH$_2$(CH$_2$)$_8$CH$_3$ and —CH$_3$, wherein at least one occurrence of R is —CH$_2$(CH$_2$)$_8$CH$_3$; and ratio of m:n:p is 3:5:2.

7. The hybrid nanomaterial according to claim 1, wherein the weight ratio of graphene oxide to cationic quaternized chitosan in the hybrid nanomaterial is in the range of about 1:2 to about 1:3.

8. The hybrid nanomaterial according to claim 1, wherein the cationic quaternized chitosan is covalently bonded to the graphene oxide via an amide bond.

9. An antimicrobial composition comprising a liquid and a hybrid nanomaterial comprising graphene oxide nanomaterial covalently conjugated to cationic quaternized chitosan, wherein the cationic quaternized chitosan prior to the conjugation is represented by formula (I)

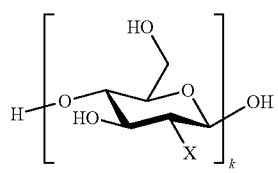

(I)

wherein

X, at each occurrence, is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$ and R$^2$ are independently selected from H and C$_{1-18}$ alkyl, R$^3$, R$^4$ and R$^5$ are each independently C$_{1-18}$ alkyl, and k is an integer from 3 to 3000; and wherein the graphene oxide nanomaterial is covalently conjugated to the cationic quaternized chitosan at an occurrence of X, wherein the occurrence of X is —NH$_2$.

10. The antimicrobial composition according to claim 9, wherein concentration of the hybrid nanomaterial ranges from about 20 μg mL$^{-1}$ to about 3000 μg mL$^{-1}$ of the composition.

11. A method of preparing a hybrid nanomaterial comprising graphene oxide nanomaterial covalently conjugated to cationic quaternized chitosan, wherein the cationic quaternized chitosan prior to the conjugation is represented by formula (I)

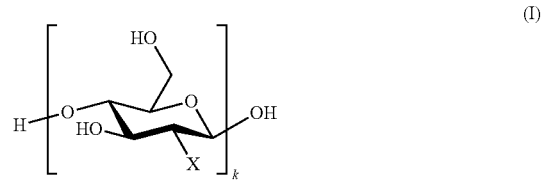

wherein

X, at each occurrence, is independently selected from —NH—C(O)—CH$_3$, —N(R$^1$)(R$^2$) and —N$^+$(R$^3$)(R$^4$)(R$^5$), provided that at least one X is —N$^+$(R$^3$)(R$^4$)(R$^5$), R$^1$ and R$^2$ are independently selected from H and C$_{1-18}$ alkyl, R$^3$, R$^4$ and R$^5$ are each independently C$_{1-18}$ alkyl, and k is an integer from 3 to 3000; and wherein the graphene oxide nanomaterial is covalently conjugated to the cationic quaternized chitosan at an occurrence of X, wherein the occurrence of X is —NH$_2$, the method comprising reacting cationic quaternized chitosan of formula (I) with graphene oxide in the presence of a coupling reagent to covalently bond the cationic quaternized chitosan to the graphene oxide.

12. The method according to claim 11, wherein R$^1$ and R$^2$ are selected from H and C$_{1-18}$ alkyl; and R$^3$, R$^4$, and R$^5$ are each independently C$_{1-10}$ alkyl.

13. The method according to claim 12, wherein R$^3$ and R$^4$ are methyl and R$^5$ is C$_{1-10}$ alkyl.

14. The method according to claim 11, wherein the ratio of monomers with X=—N(R$^1$)(R$^2$) and X=—N$^+$(R$^3$)(R$^4$)(R$^5$) to monomers with X=—NH—C(O)—CH$_3$ is in the range of 2:1 to 5:1.

15. The method according to claim 14, wherein the ratio of monomers with X=—N(R$^1$)(R$^2$) to monomers with X=—N$^+$(R$^3$)(R$^4$)(R$^5$) is in the range of 1:4 to 4:1.

16. The method according to claim 11, wherein the cationic quaternized chitosan comprises dimethyldecylammonium chitosan having general formula (II)

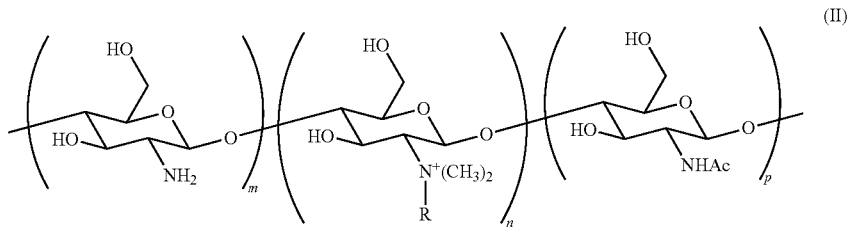

wherein

R is selected from the group consisting of —CH$_2$(CH$_2$)$_8$CH$_3$ and —CH$_3$, wherein at least one occurrence of R is —CH$_2$(CH$_2$)$_8$CH$_3$; and ratio of m:n:p is 3:5:2.

17. The method according to claim 11, wherein the coupling reagent comprises 1-ethyl-3-(3-dimethylaminopropyl) carbodiimide.

18. The method according to claim 17, wherein the coupling reagent further comprises N-hydroxysuccinimide.

19. The method according to claim 11, wherein the cationic quaternized chitosan is covalently bonded to the graphene oxide via an amide bond.

20. The method according to claim 11, wherein the weight ratio of graphene oxide to the cationic quaternized chitosan is in the range of about 1:1 to about 1:10.

* * * * *